(12) United States Patent
Miller et al.

(10) Patent No.: US 9,931,036 B2
(45) Date of Patent: Apr. 3, 2018

(54) SYSTEMS AND METHODS FOR PROCESSING AND TRANSMITTING SENSOR DATA

(71) Applicant: DexCom, Inc., San Diego, CA (US)

(72) Inventors: Thomas Miller, Valley Center, CA (US); Mark Dervaes, Carlsbad, CA (US); Phong Lieu, San Diego, CA (US); Peter C. Simpson, Encinitas, CA (US); Shawn Larvenz, Ramona, CA (US); Jacob S. Leach, San Diego, CA (US); Sebastian Bohm, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 510 days.

(21) Appl. No.: 14/142,677

(22) Filed: Dec. 27, 2013

(65) Prior Publication Data

US 2014/0266776 A1 Sep. 18, 2014

Related U.S. Application Data

(63) Continuation-in-part of application No. 13/830,330, filed on Mar. 14, 2013, which is a continuation of application No. 13/827,577, filed on Mar. 14, 2013.

(51) Int. Cl.
*G08C 19/16* (2006.01)
*A61B 5/00* (2006.01)
(Continued)

(52) U.S. Cl.
CPC .......... *A61B 5/0015* (2013.01); *A61B 5/0002* (2013.01); *A61B 5/076* (2013.01);
(Continued)

(58) Field of Classification Search
CPC .................................................... A61B 5/4866
See application file for complete search history.

(56) References Cited

U.S. PATENT DOCUMENTS

| 6,950,708 B2 | 9/2005 | Bowman et al. |
| 6,958,705 B2 | 10/2005 | Label et al. |

(Continued)

FOREIGN PATENT DOCUMENTS

| EP | 2453398 A1 | 5/2012 |
| WO | WO 1997-018639 | 5/1997 |

(Continued)

OTHER PUBLICATIONS

Mirano° Systems 2012. Green Receipt. https://web.archive.org/web/20121224003730/http://mirano.ca/.

*Primary Examiner* — Amine Benlagsir
(74) *Attorney, Agent, or Firm* — Knobbe, Martens, Olson & Bear, LLP

(57) ABSTRACT

Systems and methods for processing, transmitting and displaying data received from an analyte sensor, such as a glucose sensor, are disclosed. In an embodiment, a method for transmitting data between a first communication device associated with an analyte sensor and a second communication device configured to provide user access to sensor-related information comprises: activating a transceiver of a first communication device associated with an analyte sensor at a first time; and establishing a two-way communication channel with the second communication device; wherein the activating comprises waking the transceiver from a low power sleep mode using a forced wakeup from the second communication device.

12 Claims, 14 Drawing Sheets

(51) Int. Cl.
  *G06F 19/00*  (2018.01)
  *A61B 5/145*  (2006.01)
  *A61B 5/07*  (2006.01)

(52) U.S. Cl.
  CPC ...... *A61B 5/14503* (2013.01); *A61B 5/14532* (2013.01); *A61B 5/742* (2013.01); *A61B 5/7475* (2013.01); *G06F 19/3412* (2013.01); *G06F 19/3418* (2013.01); *A61B 2560/0209* (2013.01); *G06F 19/3468* (2013.01)

(56) References Cited

U.S. PATENT DOCUMENTS

| | | |
|---|---|---|
| 7,171,274 B2 | 1/2007 | Starkweather et al. |
| 7,643,798 B2 | 1/2010 | Ljung |
| 8,073,008 B2 | 12/2011 | Mehta et al. |
| 8,095,692 B2 | 1/2012 | Mehta et al. |
| 8,112,240 B2 | 2/2012 | Fennell |
| 8,121,857 B2 | 2/2012 | Galasso et al. |
| 8,208,973 B2 | 6/2012 | Mehta |
| 2005/0038332 A1 | 2/2005 | Saidara et al. |
| 2007/0060093 A1 | 3/2007 | Kerth et al. |
| 2007/0060132 A1* | 3/2007 | Wilhelmsson ...... H04W 52/325 455/445 |
| 2007/0163880 A1 | 7/2007 | Woo et al. |
| 2007/0253021 A1 | 11/2007 | Mehta et al. |
| 2008/0199894 A1 | 8/2008 | Galasso |
| 2009/0036760 A1 | 2/2009 | Hayter |
| 2009/0156924 A1 | 6/2009 | Shariati et al. |
| 2009/0171180 A1 | 7/2009 | Pering et al. |
| 2009/0192366 A1 | 7/2009 | Mensinger et al. |
| 2009/0192751 A1 | 7/2009 | Kamath et al. |
| 2009/0289507 A1 | 11/2009 | Shiu et al. |
| 2009/0291634 A1 | 11/2009 | Sarrisalo |
| 2010/0026250 A1 | 2/2010 | Petty et al. |
| 2010/0198034 A1 | 8/2010 | Thomas et al. |
| 2010/0292556 A1 | 11/2010 | Golden |
| 2010/0323431 A1 | 12/2010 | Rutkowski et al. |
| 2011/0019824 A1 | 1/2011 | Sattiraju et al. |
| 2011/0022411 A1 | 1/2011 | Hjelm et al. |
| 2011/0054282 A1 | 3/2011 | Nekoomaram et al. |
| 2011/0058485 A1 | 3/2011 | Sloan |
| 2011/0060530 A1 | 3/2011 | Fennell |
| 2011/0264035 A1* | 10/2011 | Yodfat ............... A61M 5/14248 604/66 |
| 2012/0078071 A1 | 3/2012 | Bohm et al. |
| 2012/0216507 A1 | 8/2012 | VanNieuwstadt |
| 2012/0235823 A1 | 9/2012 | Trock et al. |
| 2013/0137946 A1* | 5/2013 | Geske ................ A61B 5/02433 600/324 |
| 2013/0172709 A1 | 7/2013 | Mears et al. |
| 2013/0203351 A1 | 8/2013 | Hillan et al. |
| 2014/0235166 A1 | 8/2014 | Molettiere et al. |

FOREIGN PATENT DOCUMENTS

| | | | |
|---|---|---|---|
| WO | WO 9718639 A1 * | 5/1997 | ........... A61B 5/0006 |
| WO | WO 2013-0019225 | 2/2013 | |

\* cited by examiner

SYSTEMS AND METHODS FOR PROCESSING AND TRANSMITTING SENSOR DATA

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation-in-part of U.S. application Ser. No. 13/830,330, filed on Mar. 14, 2013, which is a continuation of U.S. application Ser. No. 13/827,577, filed on Mar. 14, 2013, the disclosures of which are hereby expressly incorporated by reference in their entirety and are hereby expressly made a portion of this application.

FIELD

The present invention relates generally to systems and methods for processing, transmitting and displaying data received from an analyte sensor, such as a glucose sensor.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is going up (higher) or down (lower) based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

In a first aspect, a method for transmitting data between a first communication device associated with an analyte sensor and a second communication device configured to provide user access to sensor-related information is disclosed, the method comprising: activating a transceiver of a first communication device associated with an analyte sensor at a first time; and establishing a two-way communication channel with the second communication device; wherein the activating comprises waking the transceiver from a low power sleep mode using a forced wakeup from the second communication device. In an embodiment of the first aspect, establishing the two-way communication channel includes using authentication information related to the transceiver. In an embodiment of the first aspect, authentication information comprises a transmitter serial number. In an embodiment of the first aspect, the transceiver of the first communication device is configured to engage in near field communication (NFC) with second communication device. In an embodiment of the first aspect, the transceiver of the first communication device comprises an NFC tag that may be powered by the second communication device. In an embodiment of the first aspect, the second communication device is configured to engage in NFC with the transceiver of the first communication device and wherein the second communication device comprises an NFC initiator. In an embodiment of the first aspect, the second communication device comprises a software application that allows a user to initiate NFC with the first communication device. In an embodiment of the first aspect, the software application instructs the user to place second communication in close proximity to the first communication device. In an embodiment of the first aspect, close proximity comprises a distance that is less than 12 inches. In an embodiment of the first aspect, close proximity comprises a distance that is less than 6 inches. In an embodiment of the first aspect, the method further comprises: sending sensor-related information to the second communication device using the two-way communication channel during a transmission window; deactivating the transceiver of the first communication device at a second time; and periodically repeating the activating, establishing, sending and deactivating, wherein a difference between the first time and the second time is less than or equal to one minute, and wherein the periodic repeating is performed at least once every 30 minutes. In an embodiment of the first aspect, the forced wakeup is out of sync with the periodic activating and deactivating, causing a break in a transmission window. In an embodiment of the first aspect, the method further comprises: sending a calibration value to the first communication device and receiving an updated glucose value at the second communication device immediately thereafter. In an embodiment of the first aspect, the method further comprises: sending new setting information to the first communication device. In an embodiment of the first aspect, the first communication device and second communication device are paired using NFC.

In a second aspect, a method of providing a transmission pause mode is disclosed, the method comprising: sending a transmission pause command from a second communication device to a first communication device, wherein the first communication device is in communication with analyte sensor circuitry. In an embodiment of the second aspect, a software application running on the second communication device prompts the user to enter the transmission pause mode, the transmission pause mode having a reduced power level. In an embodiment of the second aspect, the transmission pause mode is in compliance with the federal aviation administration guidelines for electronic devices. In an embodiment of the second aspect, the user is requested to enter a duration of time that the first communication device will remain in the transmission pause mode. In an embodiment of the second aspect, the second communication device deactivates the transceiver of the first communication device for the transmission pause mode duration.

In a third aspect, a method for detecting sleep current in a sensor device using a sleep current circuit in communication with the sensor device is disclosed, the method comprising: initiating a reduced power state for the sensor device; providing a sleep pulse signal to a capacitor in the sleep current circuit; measuring a charge on the capacitor in the sleep current circuit; and comparing the charge on the capacitor to a predetermined threshold to determine if the charge on the capacitor exceeds the predetermined threshold. In an embodiment of the third aspect, the method further comprises: terminating the reduced power state for the sensor device. In an embodiment of the third aspect, the measuring a charge on the capacitor is performed after the reduced power state is terminated. In an embodiment of the third aspect, the method further comprises: terminating the sleep pulse signal while the sensor device is in a reduced power state. In an embodiment of the third aspect, the method further comprises: terminating the reduced power state for the sensor device within 1 second of terminating the sleep pulse signal. In an embodiment of the third aspect, the sleep pulse signal is provided to the capacitor via a switch. In an embodiment of the third aspect, the predetermined threshold is an expected charge on the capacitor that correlates with the sleep pulse signal. In an embodiment of the third aspect, the sleep current is any unexpected current flowing within the sensor device while it is in the reduced power state. In an embodiment of the third aspect, the sleep current is detected by subtracting the predetermined threshold from the charge on the capacitor. In an embodiment of the third aspect, the method further comprises: providing an error message to a user if sleep current is detected.

In a fourth aspect, a system for measuring sleep current is disclosed, the system comprising: sensor measurement circuitry in communication with one or more power supply circuitry configured to provide power to the measurement circuitry; sleep current circuitry configured to detect sleep current in the system; and control circuitry configured to provide instructions to measurement circuitry to switch to a sleep mode and configured to provide a sleep pulse signal to the sleep current circuitry for determining if any sleep current is present in the system. In an embodiment of the fourth aspect, the sleep current circuitry comprises a capacitor configured to collect a charge that correlates with the sleep pulse signal. In an embodiment of the fourth aspect, the sleep current circuitry is configured to detect sleep current by comparing the charge on the capacitor with a predetermined threshold.

In a fifth aspect, a method of providing an adjustable integration window is disclosed, the method comprising: storing two or more sensor data points in a memory buffer to create an integrated data point, wherein each of the sensor data points is associated with a time stamp and the stored data points define an integration window; receiving a reference value associated with a time stamp; and adjusting the integration window to correspond to the time stamp for the reference value. In an embodiment of the fifth aspect, the integration window comprises two or more sensor data points taken at 30-second time intervals. In an embodiment of the fifth aspect, the integration window comprises ten sensor data points taken at 30-second time intervals. In an embodiment of the fifth aspect, the two or more sensor data points are averaged to create an integrated data point. In an embodiment of the fifth aspect, wherein upon receipt of a new sensor data point, the sensor data point associated with an oldest time stamp stored in the memory buffer is deleted, and the sensor data points stored in the memory buffer and the new sensor data point are averaged to create an integrated data point. In an embodiment of the fifth aspect, the reference value is a blood glucose value. In an embodiment of the fifth aspect, adjusting the integration window to correspond to the time stamp for the reference value comprises: selecting an even number of sensor data points having time stamps before and after the time stamp associated with the reference value; and averaging the sensor data points to provide an integrated data point having a close time proximity to the time stamp associated with the reference value. In an embodiment of the fifth aspect, the time proximity of the integrated data point is within thirty seconds of the time stamp associated with the reference value. In an embodiment of the fifth aspect, the sensor data points closest in time to the time stamp for the reference value are more heavily weighted than sensor data points furthest from the time stamp for the reference value in the integration window. In an embodiment of the fifth aspect, the integrated data point is extrapolated using one or more sensor data points stored in the memory buffer. In an embodiment of the fifth aspect, the integrated data point is extrapolated to a point of 2.5 minutes in the future using five 30-second data values stored in the memory buffer. In an embodiment of the fifth aspect, the sensor data points defining the integration window are taken at a fixed time interval, wherein the fixed time interval is adjusted depending on sensor data information. In an embodiment of the fifth aspect, sensor data information comprises a glucose rate of change.

In a sixth aspect, a method of providing leak detection adjustment is disclosed, the method comprising: detecting a leakage current using a leak detection circuit in communication with an analyte sensor system having a processor; receiving, using the processor, the leakage current from the leak detection circuit; and performing an adjustment to a sensor signal using the leakage current. In an embodiment of the sixth aspect, the adjustment to the sensor signal comprises subtracting the leakage current from the sensor signal. In an embodiment of the sixth aspect, performing an adjustment to the sensor signal is performed using the processor of the analyte sensor system. In an embodiment of the sixth aspect, performing an adjustment to the sensor signal is performed using an external processing device. In an embodiment of the sixth aspect, the method further comprises: providing the adjusted sensor signal to a user.

In a seventh aspect, a method, system or computer software product for transmitting data between devices of an analyte monitoring system is provided. The method system or computer software product comprises: generating sensor data using a sensor electronics module electrically connected to a continuous analyte sensor; establishing a two-way communication channel between the sensor electronics module and the a display device and each of the sensor electronics module and display device transmitting at a first transmission power; and initiating a low power transmission mode responsive to receiving user input at user interface of the display device indicative of entering the mode, wherein the low power transmission mode comprises one or both of the sensor electronics module and the display device transmitting at a second transmission power that is lower than the first transmission power.

In some implementations, the seventh aspect may include one or more of the following: wherein the initiating comprises the display device sending a command to the sensor electronics module to enter the low power mode; wherein the display device prompts a user to input a duration of time for the low power transmission mode, and wherein the display device and the sensor electronics module automatically exit the low power transmission mode after expiration of the duration of time; further comprising initiating the low power transmission mode responsive to receiving user input indicative of starting the low power transmission mode, and exiting the low power transmission mode responsive to receiving user input indicative of ending the low power transmission mode; wherein the user input comprises sensing user selection of a user-selectable button on the user interface of the display device; and wherein the second transmission power is in the range of about 25%-75% lower than the first transmission power.

DETAILED DESCRIPTION

Figure 1:
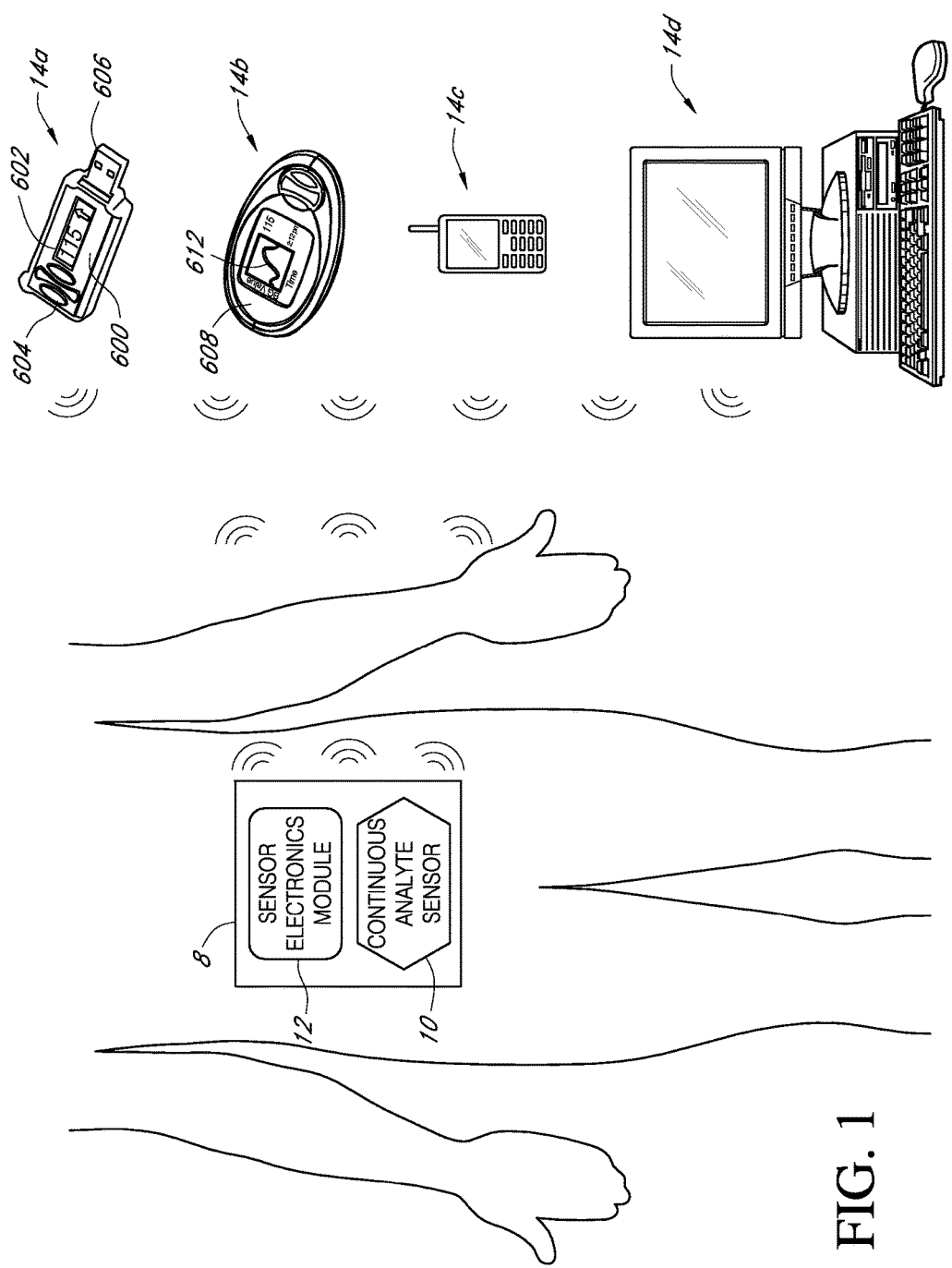
FIG. 1 is a diagram illustrating some embodiments of a continuous analyte sensor system including a sensor electronics module.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the systems and methods discussed herein, a number of terms are defined below. The terms defined below, as well as other terms used herein, should be construed to include the provided definitions, the ordinary and customary meaning of the terms, and any other implied meaning for the respective terms. Thus, the definitions below do not limit the meaning of these terms, but only provide exemplary definitions.

The terms "processor module," "microprocessor" and "processor" as used herein are broad terms and are to be given their ordinary and customary meaning to a person of ordinary skill in the art, and furthermore refer without limitation to a computer system, state machine, and the like that performs arithmetic and logic operations using logic circuitry that responds to and processes the basic instructions that drive a computer.

The terms "sensor data", as used herein is a broad term and is to be given its ordinary and customary meaning to a person of ordinary skill in the art, and furthermore refers without limitation to any data associated with a sensor, such as a continuous analyte sensor. Sensor data includes a raw data stream, or simply data stream, of analog or digital signal directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The term broadly encompasses a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "algorithm" as used herein is a broad term and is to be given its ordinary and customary meaning to a person of ordinary skill in the art, and furthermore refers without limitation to a computational process (associated with computer programming or other written instructions) involved in transforming information from one state to another.

The term "sensor" as used herein is a broad term and is to be given its ordinary and customary meaning to a person of ordinary skill in the art, and furthermore refers without limitation to any device (or portion of a device) that measures a physical quantity and converts it into a signal that can be processed by analog and/or digital circuitry. Thus, the output of a sensor may be an analog and/or digital signal.

Examples of sensors include analyte sensors, glucose sensors, temperature sensors, altitude sensors, accelerometers, and heart rate sensors.

The terms "coupled", "operably connected" and "operably linked" as used herein are broad terms and are to be given their ordinary and customary meaning to a person of ordinary skill in the art, and furthermore refer without limitation to one or more components being linked to another component(s), either directly or indirectly, in a manner that allows transmission of signals between the components. For example, modules of a computing device that communicate via a common data bus are coupled to one another. As another example, one or more electrodes of a glucose sensor can be used to detect the amount of glucose in a sample and convert that information into a signal, e.g., an electrical or electromagnetic signal; the signal can then be transmitted to an electronic circuit. In this case, the electrode is "operably linked" to the electronic circuitry, even though the analog signal from the electrode is transmitted and/or transformed by analog and/or digital circuitry before reaching the electronic circuit. These terms are broad enough to include wireless connectivity.

The term "physically connected" as used herein is a broad term and is to be given its ordinary and customary meaning to a person of ordinary skill in the art, and furthermore refers without limitation to one or more components that are connected to another component(s) through direct contact and/or a wired connection, including connecting via one or more intermediate physically connecting component(s). For example, a glucose sensor may be physically connected to a sensor electronics module, and thus the processor module located therein, either directly or via one or more electrical connections.

The term "continuous analyte sensor" as used herein is a broad term and is to be given its ordinary and customary meaning to a person of ordinary skill in the art, and furthermore refers without limitation to a device, or portion of a device, that continuously or continually measures a concentration of an analyte, for example, at time intervals ranging from fractions of a second up to, for example, 1, 2, or 5 minutes, or longer. In one exemplary embodiment, a glucose sensor comprises a continuous analyte sensor, such as is described in U.S. Pat. No. 7,310,544, which is incorporated herein by reference in its entirety.

The term "sensor session" as used herein, is a broad term and is to be given its ordinary and customary meaning to a person of ordinary skill in the art, and refers without limitation to a period of time a sensor is in use, such as but not limited to a period of time starting at the time the sensor is implanted (e.g., by the host) to removal of the sensor (e.g., removal of the sensor from the host's body and/or removal of the sensor electronics module from the sensor housing).

The term "sensor information" as used herein is a broad term, and is to be given its ordinary and customary meaning to a person of ordinary skill in the art, and furthermore refers without limitation to information associated with measurement, signal processing (including calibration), alarms, data transmission, and/or display associated with a sensor, such as a continuous analyte sensor. The term is broad enough to include raw sensor data (one or more raw analyte concentration values), as well as transformed sensor data. In some embodiments, sensor information includes displayable sensor information.

The term "displayable sensor information" as used herein is a broad term, and is to be given its ordinary and customary meaning to a person of ordinary skill in the art, and furthermore refers without limitation to information that is transmitted for display on one or more display devices. As is discussed elsewhere herein, the content of displayable sensor information that is transmitted to a particular display device may be customized for the particular display device. Additionally, formatting of displayable sensor information may be customized for respective display devices. Displayable sensor information may include any sensor data, including raw sensor data, transformed sensor data, and/or any information associated with measurement, signal processing (including calibration), and/or alerts associated with one or more sensors.

The term "data package" as used herein is a broad term, and is to be given its ordinary and customary meaning to a person of ordinary skill in the art, and furthermore refers without limitation to a combination of data that is transmitted to one or more display devices, such as in response to triggering of an alert. A data package may include displayable sensor information (e.g., that has been selected and formatted for a particular display device) as well as header information, such as data indicating a delivery address, communication protocol, etc. Depending on the embodiment, a data package may comprises multiple packets of data that are separately transmitted to a display device (and reassembled at the display device) or a single block of data that is transmitted to the display device. Data packages may be formatted for transmission via any suitable communication protocol, including radio frequency, Bluetooth, universal serial bus, any of the wireless local area network (WLAN) communication standards, including the IEEE 802.11, 802.15, 802.20, 802.22 and other 802 communication protocols, and/or a proprietary communication protocol.

The term "direct wireless communication" as used herein is a broad term, and is to be given its ordinary and customary meaning to a person of ordinary skill in the art, and furthermore refers without limitation to a data transmission that goes from one device to another device without any intermediate data processing (e.g., data manipulation). For example, direct wireless communication between a sensor electronics module and a display device occurs when the sensor information transmitted from the sensor electronics module is received by the display device without intermediate processing of the sensor information. The term is broad enough to include wireless communication that is transmitted through a router, a repeater, a telemetry receiver (e.g., configured to re-transmit the sensor information without additional algorithmic processing), and the like. The term is also broad enough to include transformation of data format (e.g., via a Bluetooth receiver) without substantive transformation of the sensor information itself.

Overview

In some embodiments, a system is provided for continuous measurement of an analyte in a host that includes: a continuous analyte sensor configured to continuously measure a concentration of the analyte in the host and a sensor electronics module physically connected to the continuous analyte sensor during sensor use. In some embodiments, the sensor electronics module includes electronics configured to process a data stream associated with an analyte concentration measured by the continuous analyte sensor in order to generate sensor information that includes raw sensor data, transformed sensor data, and/or any other sensor data, for example. The sensor electronics module may further be configured to generate sensor information that is customized for respective display devices, such that different display devices may receive different sensor information.

Display Devices

In some embodiments, the sensor electronics module is configured to search for and/or attempt wireless communication with a display device from a list of display devices. In some embodiments, the sensor electronics module is configured to search for and/or attempt wireless communication with a list of display devices in a predetermined and/or programmable order (e.g., grading and/or escalating), for example, wherein a failed attempt at communication with and/or alarming with a first display device triggers an attempt at communication with and/or alarming with a second display device, and so on.

Depending on the embodiment, one or more display devices that receive data packages from the sensor electronics module are "dummy displays", wherein they display the displayable sensor information received from the sensor electronics module without additional processing (e.g., prospective algorithmic processing necessary for real-time display of sensor information). In some embodiments, the displayable sensor information comprises transformed sensor data that does not require processing by the display device prior to display of the displayable sensor information. Some display devices may comprise software including display instructions (software programming comprising instructions configured to display the displayable sensor information and optionally query the sensor electronics module to obtain the displayable sensor information) configured to enable display of the displayable sensor information thereon. In some embodiments, the display device is programmed with the display instructions at the manufacturer and can include security and/or authentication to avoid plagiarism of the display device. In some embodiments, a display device is configured to display the displayable sensor information via a downloadable program (for example, a downloadable Java Script via the internet), such that any display device that supports downloading of a program (for example, any display device that supports Java applets) therefore can be configured to display displayable sensor information (e.g., mobile phones, PDAs, PCs and the like).

In some embodiments, certain display devices may be in direct wireless communication with the sensor electronics module, however intermediate network hardware, firmware, and/or software can be included within the direct wireless communication. In some embodiments, a repeater (e.g., a Bluetooth repeater) can be used to re-transmit the transmitted displayable sensor information to a location farther away than the immediate range of the telemetry module of the sensor electronics module, wherein the repeater enables direct wireless communication when substantive processing of the displayable sensor information does not occur. In some embodiments, a receiver (e.g., Bluetooth receiver) can be used to re-transmit the transmitted displayable sensor information, possibly in a different format, such as in a text message onto a TV screen, wherein the receiver enables direct wireless communication when substantive processing of the sensor information does not occur. In some embodiments, the sensor electronics module directly wirelessly transmits displayable sensor information to one or a plurality of display devices, such that the displayable sensor information transmitted from the sensor electronics module is received by the display device without intermediate processing of the displayable sensor information.

In some embodiments, one or more display devices comprise built-in authentication mechanisms, wherein authentication is required for communication between the sensor electronics module and the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the display devices can be accomplished by the user and/or manufacturer via the password. However, any known authentication system or method useful for telemetry devices can be used.

In some embodiments, one or more display devices are configured to query the sensor electronics module for displayable sensor information, wherein the display device acts as a master device requesting sensor information from the sensor electronics module (e.g., a slave device) on-demand, for example, in response to a query. In some embodiments, the sensor electronics module is configured for periodic, systematic, regular, and/or periodic transmission of sensor information to one or more display devices (for example, every 1, 2, 5, or 10 minutes or more). In some embodiments, the sensor electronics module is configured to transmit data packages associated with a triggered alert (e.g., triggered by one or more alert conditions). However, any combination of the above described statuses of data transmission can be implemented with any combination of paired sensor electronics module and display device(s). For example, one or more display devices can be configured for querying the sensor electronics module database and for receiving alarm information triggered by one or more alarm conditions being met. Additionally, the sensor electronics module can be configured for periodic transmission of sensor information to one or more display devices (the same or different display devices as described in the previous example), whereby a system can include display devices that function differently with regard to how they obtain sensor information.

In some embodiments, as described in more detail elsewhere herein, a display device is configured to query the data storage memory in the sensor electronics module for certain types of data content, including direct queries into a database in the sensor electronics module's memory and/or requests for configured or configurable packages of data content therefrom; namely, the data stored in the sensor electronics module is configurable, queryable, predetermined, and/or pre-packaged, based on the display device with which the sensor electronics module is communicating. In some additional or alternative embodiments, the sensor electronics module generates the displayable sensor information based on its knowledge of which display device is to receive a particular transmission. Additionally, some display devices are capable of obtaining calibration information and wirelessly transmitting the calibration information to the sensor electronics module, such as through manual entry of the calibration information, automatic delivery of the calibration information, and/or an integral reference analyte monitor incorporated into the display device. U.S. Patent Publication Nos. 2006/0222566, 2007/0203966, 2007/0208245, and 2005/0154271, all of which are incorporated herein by reference in their entirety, describe systems and methods for providing an integral reference analyte monitor incorporated into a display device and/or other calibration methods that can be implemented with the disclosed embodiments.

In general, a plurality of display devices (e.g., a small (key fob) display device, a larger (hand-held) display device, a mobile phone, a reference analyte monitor, a drug delivery device, a medical device and a personal computer) are configured to wirelessly communicate with the sensor electronics module, wherein the one or more display devices are configured to display at least some of the displayable sensor information wirelessly communicated from the sensor electronics module, wherein displayable sensor information includes sensor data, such as raw data and/or transformed sensor data, such as analyte concentration values, rate of change information, trend information, alert information, sensor diagnostic information and/or calibration information, for example.

Small (Key Fob) Display Device

In some embodiments, one the plurality of display devices is a small (e.g., key fob) display device 14a (FIG. 1) that is configured to display at least some of the sensor information, such as an analyte concentration value and a trend arrow. In general, a key fob device is a small hardware device with a built-in authentication mechanism sized to fit on a key chain. However, any small display device 14a can be configured with the functionality as described herein with reference to the key fob device 14a, including a wrist band, a hang tag, a belt, a necklace, a pendent, a piece of jewelry, an adhesive patch, a pager, an identification (ID) card, and the like, all of which are included by the phrase "small display device" and/or "key fob device" herein.

In general, the key fob device 14a includes electronics configured to receive and display displayable sensor information. In some embodiments, the electronics include a RAM and a program storage memory configured at least to display the sensor data received from the sensor electronics module. In some embodiments, the key fob device 14a includes an alarm configured to warn a host of a triggered alert (e.g., audio, visual and/or vibratory). In some embodiments, the key fob device 14a includes a user interface, such as an LCD 602 and one or more buttons 604 that allows a user to view data, such as a numeric value and/or an arrow, to toggle through one or more screens, to select or define one or more user parameters, to respond to (e.g., silence, snooze, turn off) an alert, and/or the like.

In some embodiments, the key fob display device has a memory (e.g., such as in a gig stick or thumb drive) that stores sensor, drug (e.g., insulin) and other medical information, enabling a memory stick-type function that allows data transfer from the sensor electronics module to another device (e.g., a PC) and/or as a data back-up location for the sensor electronics module memory (e.g., data storage memory). In some embodiments, the key fob display device is configured to be automatically readable by a network system upon entry into a hospital or other medical complex.

In some embodiments, the key fob display device includes a physical connector, such as USB port 606, to enable connection to a port (e.g., USB) on a computer, enabling the key fob to function as a data download device (e.g., from the sensor electronics module to a PC), a telemetry connector (e.g., Bluetooth adapter/connector for a PC), and/or enables configurable settings on the key fob device (e.g., via software on the PC that allows configurable parameters such as numbers, arrows, trend, alarms, font, etc.). In some embodiments, user parameters associated with the small (key fob) display device can be programmed into (and/or modified) by a display device such as a personal computer, personal digital assistant, or the like. In some embodiments, user parameters include contact information, alert/alarms settings (e.g., thresholds, sounds, volume, and/or the like), calibration information, font size, display preferences, defaults (e.g., screens), and/or the like. Alternatively, the small (key fob) display device can be configured for direct programming of user parameters. In some embodiments, wherein the small (key fob) display device comprises a telemetry module, such as Bluetooth, and a USB connector (or the like), such that the small (key fob) display device additionally functions as telemetry adapter (e.g., Bluetooth adapter) enabling direct wireless communication between the sensor electronics module and the PC, for example, wherein the PC does not include the appropriate telemetry adapter therein.

Large (Hand-held) Display Device

In some embodiments, one the plurality of display devices is a hand-held display device 14b (FIG. 1) configured to display sensor information including an analyte concentration and a graphical representation of the analyte concentration over time. In general, the hand-held display device comprises a display 608 sufficiently large to display a graphical representation 612 of the sensor data over a time period, such as a previous 1, 3, 5, 6, 9, 12, 18, or 24-hours of sensor data. In some embodiments, the hand-held device 14b is configured to display a trend graph or other graphical representation, a numeric value, an arrow, and/or to alarm the host. U.S. Patent Publication No. 2005/0203360, which is incorporated herein by reference in its entirety, describes and illustrates some examples of display of data on a hand-held display device. Although FIG. 1 illustrates some embodiments of a hand-held display device 14b, the hand-held device can be any single application device or multi-application device, such as mobile phone, a palm-top computer, a PDA, portable media player (e.g., iPod, MP3 player), a blood glucose meter, an insulin pump, and/or the like.

In some embodiments, a mobile phone (or PDA) 14c is configured to display (as described above) and/or relay sensor information, such as via a voice or text message to the host and/or the host's care provider. In some embodiments, the mobile phone 14c further comprises an alarm configured to warn a host of a triggered alert, such as in response to receiving a data package indicating triggering of the alert. Depending on the embodiment, the data package may include displayable sensor information, such as an on-screen message, text message, and/or pre-generated graphical representation of sensor data and/or transformed sensor data, as well as an indication of an alarm, such as an auditory alarm or a vibratory alarm, that should be activated by the mobile phone.

In some embodiments, one of the display devices is a drug delivery device, such as an insulin pump and/or insulin pen, configured to display sensor information. In some embodiments, the sensor electronics module is configured to wirelessly communicate sensor diagnostic information to the drug delivery device in order to enable to the drug delivery device to consider (include in its calculations/algorithms) a quality, reliability and/or accuracy of sensor information for closed loop and/or semi-closed loop systems, which are described in more detail in U.S. Patent Publication No. 2005/0192557, which is incorporated herein by reference in its entirety. In some alternative embodiments, the sensor electronic module is configured to wirelessly communicate with a drug delivery device that does not include a display, for example, in order to enable a closed loop and/or semi-closed loop system as described above.

In some embodiments, one of the display devices is a drug delivery device is a reference analyte monitor, such as a blood glucose meter, configured to measure a reference analyte value associated with an analyte concentration in a biological sample from the host.

Personal Computer Display Device

In some embodiments, one of the display devices is personal computer (PC) 14d (FIG. 1) configured to display sensor information. Preferably, the PC 14d has software installed, wherein the software enables display and/or performs data analysis (retrospective processing) of the historic sensor information. In some embodiments, a hardware device can be provided (not shown), wherein the hardware device (e.g., dongle/adapter) is configured to plug into a port on the PC to enable wireless communication between the sensor electronics module and the PC. In some embodiments, the PC 14*d* is configured to set and/or modify configurable parameters of the sensor electronics module 12 and/or small (key fob device) 14*a*, as described in more detail elsewhere herein.

Other Display Devices

In some embodiments, one of the display devices is an on-skin display device that is splittable from, releasably attached to, and/or dockable to the sensor housing (mounting unit, sensor pod, or the like). In some embodiments, release of the on-skin display turns the sensor off; in other embodiments, the sensor housing comprises sufficient sensor electronics to maintain sensor operation even when the on-skin display is released from the sensor housing.

In some embodiments, one of the display devices is a secondary device, such as a heart rate monitor, a pedometer, a temperature sensor, a car initialization device (e.g., configured to allow or disallow the car to start and/or drive in response to at least some of the sensor information wirelessly communicated from the sensor electronics module (e.g., glucose value above a predetermined threshold)). In some alternative embodiments, one of the display devices is designed for an alternative function device (e.g., a caller id device), wherein the system is configured to communicate with and/or translate displayable sensor information to a custom protocol of the alternative device such that displayable sensor information can be displayed on the alternative function device (display of caller id device).

Exemplary Configurations

FIG. 1 is a diagram illustrating some embodiments of a continuous analyte sensor system 8 including a sensor electronics module 12. In the embodiment of FIG. 1, the system includes a continuous analyte sensor 10 physically connected to a sensor electronics module 12, which is in direct wireless communication with a plurality of different display devices 14.

In some embodiments, the sensor electronics module 12 includes electronic circuitry associated with measuring and processing the continuous analyte sensor data, including prospective algorithms associated with processing and calibration of the sensor data. The sensor electronics module 12 may be physically connected to the continuous analyte sensor 10 and can be integral with (non-releasably attached to) or releasably attachable to the continuous analyte sensor 10. The sensor electronics module 12 may include hardware, firmware, and/or software that enables measurement of levels of the analyte via a glucose sensor, such as an analyte sensor. For example, the sensor electronics module 12 can include a potentiostat, a power source for providing power to the sensor, other components useful for signal processing and data storage, and a telemetry module for transmitting data from the sensor electronics module to one or more display devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The sensor electronics module 12 includes sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety.

Referring again to FIG. 1, a plurality of display devices 14 are configured for displaying (and/or alarming) the displayable sensor information that has been transmitted by the sensor electronics module 12 (e.g., in a customized data package that is transmitted to the display devices based on their respective preferences). For example, the display devices are configured to display the displayable sensor information as it is communicated from the sensor electronics module (e.g., in a data package that is transmitted to respective display devices), without any additional prospective processing required for calibration and real-time display of the sensor data.

Because different display devices provide different user interfaces, content of the data packages (e.g., amount, format, and/or type of data to be displayed, alarms, and the like) can be customized (e.g., programmed differently by the manufacture and/or by an end user) for each particular display device. Accordingly, in the embodiment of FIG. 1, a plurality of different display devices are in direct wireless communication with the sensor electronics module (e.g., such as an on-skin sensor electronics module 12 that is physically connected to the continuous analyte sensor 10) during a sensor session to enable a plurality of different types and/or levels of display and/or functionality associated with the displayable sensor information, which is described in more detail elsewhere herein.

Continuous Sensor

In some embodiments, a glucose sensor comprises a continuous sensor, for example a subcutaneous, transdermal (e.g., transcutaneous), or intravascular device. In some embodiments, the device can analyze a plurality of intermittent blood samples. The glucose sensor can use any method of glucose-measurement, including enzymatic, chemical, physical, electrochemical, spectrophotometric, polarimetric, calorimetric, iontophoretic, radiometric, immunochemical, and the like.

A glucose sensor can use any known method, including invasive, minimally invasive, and non-invasive sensing techniques (e.g., fluorescent monitoring), to provide a data stream indicative of the concentration of glucose in a host. The data stream is typically a raw data signal, which is converted into a calibrated and/or filtered data stream that is used to provide a useful value of glucose to a user, such as a patient or a caretaker (e.g., a parent, a relative, a guardian, a teacher, a doctor, a nurse, or any other individual that has an interest in the wellbeing of the host).

A glucose sensor can be any device capable of measuring the concentration of glucose. One exemplary embodiment is described below, which utilizes an implantable glucose sensor. However, it should be understood that the devices and methods described herein can be applied to any device capable of detecting a concentration of glucose and providing an output signal that represents the concentration of glucose.

In some embodiments, the analyte sensor is an implantable glucose sensor, such as described with reference to U.S. Pat. No. 6,001,067 and U.S. Patent Publication No. US-2005-0027463-A1. In another embodiment, the analyte sensor is a transcutaneous glucose sensor, such as described with reference to U.S. Patent Publication No. US-2006-

0020187-A1. In still other embodiments, the sensor is configured to be implanted in a host vessel or extracorporeally, such as is described in U.S. Patent Publication No. US-2007-0027385-A1, U.S. Patent Publication No. US-2008-0119703-A1, U.S. Patent Publication No. US-2008-0108942-A1, and U.S. Pat. No. 7,828,728. In one alternative embodiment, the continuous glucose sensor comprises a transcutaneous sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,12,939 to Colvin et al., for example. In another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al., for example.

Sensor Electronics Module

Figure 2A:
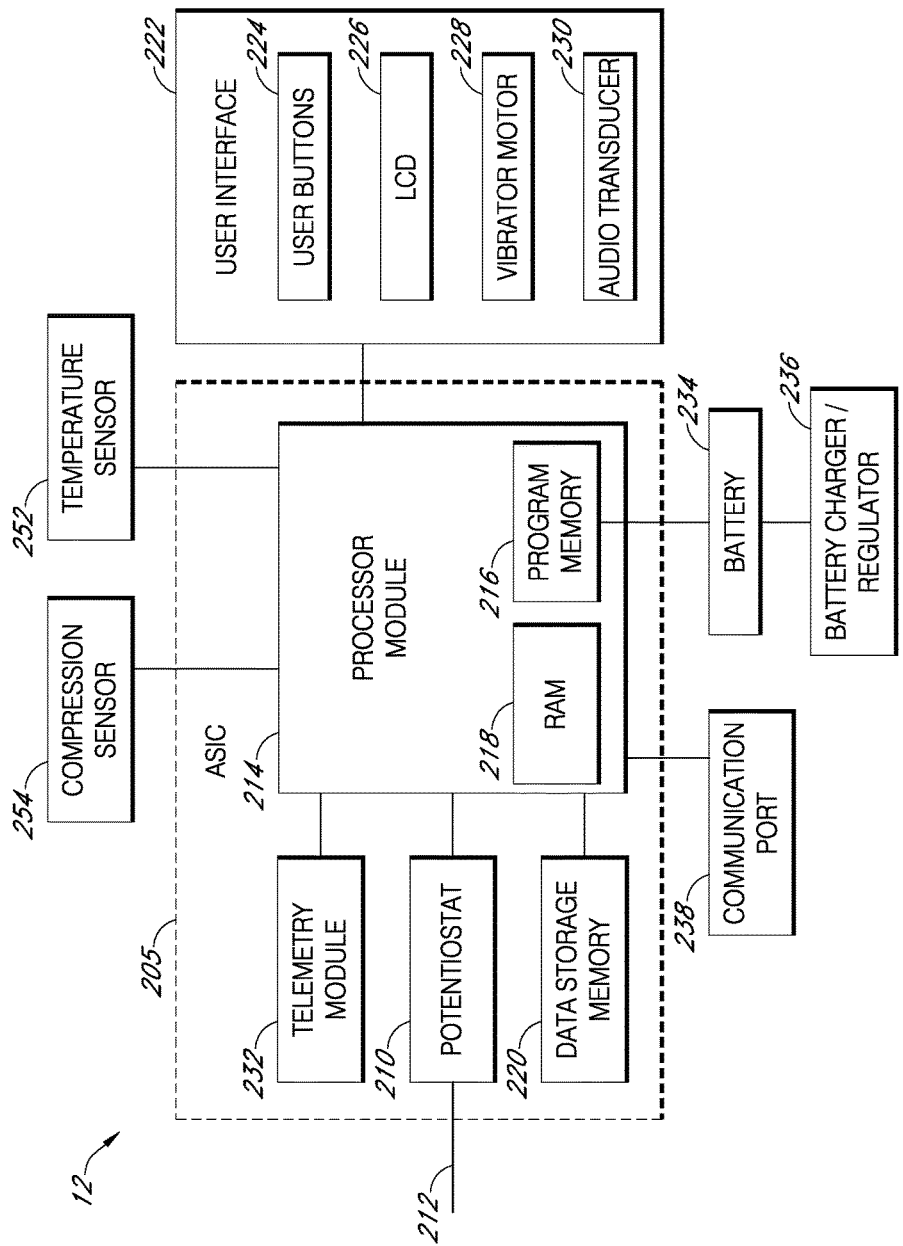
FIG. 2A is a block diagram of a sensor electronics module in accordance with some embodiments.

FIG. 2A is a block diagram illustrating embodiments of the sensor electronics module 12 (FIG. 1). The sensor electronics module 12 can include an application-specific integrated circuit (ASIC) 205, a user interface 222, compression sensor 254 and temperature sensor 252. ASIC 205 can also be coupled to a communication port 238 and a battery 234. Although FIG. 2A shows an ASIC 205 that includes much of the electronic circuitry, the ASIC 205 may be replaced with one or more of any suitable logic device, such as field programmable gate arrays (FPGA), microprocessors, analog circuitry, or other digital and/or analog circuitry. Further, ASIC 205 can include one or more additional features of sensor electronics module 12 discussed elsewhere herein, or one or more features illustrated in FIG. 2A as being part of the ASIC—such as telemetry module 232, potentiostat 210, data storage memory 220—can be separate from the ASIC.

In this embodiment, a potentiostat 210 is coupled to a glucose sensor via data line 212, for example, in order to receive sensor data from the glucose sensor. In some embodiments, the potentiostat 210 provides a voltage to the glucose sensor via a data line 212 in order to bias the sensor to enable measurement of a current value indicative of the analyte concentration in the host (also referred to as the analog portion). The potentiostat can have one channel or multiple channels (and a corresponding one or multiple data lines 212), depending on the number of working electrodes, for example. In some embodiments, the potentiostat 210 includes a resistor (not shown) that translates the current into voltage. In some embodiments, a current to frequency converter is provided that is configured to continuously integrate the measured current, for example, using a charge counting device. In some embodiments, an A/D converter digitizes the analog signal into "counts" for processing. Accordingly, the resulting raw data stream in counts is directly related to the current measured by the potentiostat 210.

A processor module 214 is the central control unit that controls the processing of the sensor electronics module 12. In some embodiments, the processor module 214 is formed as part of a custom chip, such as an ASIC, however a computer system other than an ASIC can be used to process data as described herein, for example a microprocessor can be used for some or all of the sensor electronics module processing. The processor module 214 typically provides a program memory 216, which provides semi-permanent storage of data, for example, storing data such as sensor identifier (ID) and programming to process data streams (for example, filtering, calibration, fail-safe checking, and the like). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like. In one exemplary embodiment, RAM 218 can be used for the system's cache memory, for example for temporarily storing recent sensor data.

In some embodiments, the processor module 214 comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, such as when the potentiostat 210 is configured to measure the analyte at discrete time intervals, these time intervals determine the sample rate of the digital filter. In some alternative embodiments, wherein the potentiostat 210 is configured to continuously measure the analyte, for example, using a current-to-frequency converter, the processor module 214 can be programmed to request a digital value from the integrator at a predetermined time interval, also referred to as the acquisition time. In these alternative embodiments, the values obtained by the processor module 214 are advantageously averaged over the acquisition time due the continuity of the current measurement. Accordingly, the acquisition time determines the sample rate of the digital filter.

In an embodiment, the processor module 214 may be further configured to generate data packages for transmission to one or more display devices. Furthermore, the processor module 215 may generate data packets for transmission to these outside sources, e.g., via telemetry. As discussed above, the data packages may be customizable for each display device, for example, and may include any available data, such as displayable sensor information having customized sensor data and/or transformed sensor data, sensor/sensor electronics module ID code, raw data, filtered data, calibrated data, rate of change information, trend information, error detection or correction, and/or the like.

A data storage memory 220 is operably connected to the processor module 214 and is configured to store a variety of sensor information. In some embodiments, the data storage memory stores 1, 3, 4, 5, 6, 7, 8, 9, 10, 11, 12, 13, 14, 15, 20, 30 or more days of continuous analyte sensor data. In some embodiments, the data storage memory 220 stores sensor information such as raw sensor data (one or more raw analyte concentration values), calibrated data, filtered data, transformed sensor data, and/or any other displayable sensor information.

In some embodiments, sensor electronics module 12 is configured to receive and store contact information in the data storage memory (and/or program memory), including a phone number and/or email address for the sensor's host and/or health care providers for the host (e.g., family member(s), nurse(s), doctor(s), or other health care provider(s)), which enables communication with a contact person (e.g., via phone, pager and/or text messaging in response to an alarm (e.g., a hypoglycemic alarm that has not been responded to by the host)). In some embodiments, user parameters can be programmed into (and/or modified in) the data storage memory (and/or program memory) of the sensor electronics module, via a display device such as a personal computer, personal digital assistant, or the like. Preferably, user parameters include contact information, alert/alarms settings (e.g., thresholds, sounds, volume, and/or the like), calibration information, font size, display preferences, defaults (e.g., screens), and/or the like. Alternatively, the sensor electronics module can be configured for direct programming of certain user parameters.

In one embodiment, clinical data of a medical practitioner may be uploaded to the sensor electronics module 12 and stored on the data storage memory 220, for example. Thus, information regarding the host's condition, treatments, medications, etc., may be stored on the sensor electronics module 12 and may be viewable by the host or other authorized user. In some embodiments, certain of the clinical data may be included in a data package that is transmitted to a display device in response to triggering of an alert. The clinical data may be uploaded to the sensor electronics module 12 via any available communication protocol, such as direct transmission via a wireless Bluetooth, infrared, or RF connection, or via a wired USB connection, for example. Additionally, the clinical data may be uploaded to the sensor electronics module 12 via indirect transmission, such as via one or more networks (e.g., local area, personal area, or wide area networks, or the Internet) or via a repeater device that receives the clinical data from a device of the medical practitioner and retransmits the clinical data to the sensor electronics module.

Although separate data storage 220 and program memory 216 are shown in FIG. 2A, one skilled in the art appreciates a variety of configurations, including one or multiple memories that provide the necessary storage space to support the sensor electronic module 12 data processing and storage requirements. Accordingly, the described location of storage of any particular information and/or or programming is not meant to be limiting, but rather exemplary.

In some embodiments, the sensor electronics module 12 is configured to perform smoothing and/or filtering algorithms on the sensor data (e.g., raw data stream and/or other sensor information), wherein the smoothed and/or filtered data is stored in the data storage memory as transformed data. U.S. Patent Publication No. US-2005-0043598-A1, U.S. Patent Publication No. US-2007-0032706-A1, U.S. Patent Publication No. US-2007-0016381-A1 and U.S. Patent Publication No. US-2008-0033254-A1 describe some algorithms useful in performing data smoothing and/or filtering herein (including signal artifacts replacement), and are incorporated herein by reference in their entirety.

In some embodiments, the sensor electronics module 12 is configured to calibrate the sensor data, and the data storage memory 220 stores the calibrated sensor data points as transformed sensor data. In some further embodiments, the sensor electronics module 12 is configured to wirelessly receive calibration information from a display device, from which the sensor electronics module is configured to calibrate the sensor data. U.S. Pat. Nos. 7,310,544 and 6,931,327 describe some algorithms useful in sensor calibration herein, and are incorporated herein by reference in their entirety.

In some embodiments, the sensor electronics module 12 is configured to perform additional algorithmic processing on the sensor data (e.g., calibrated and/or filtered data and/or other sensor information) and the data storage memory 220 is configured to store the transformed sensor data and/or sensor diagnostic information associated with the algorithms. U.S. Pat. Nos. 7,310,544 and 6,931,327 describe some algorithms that can be processed by the sensor electronics module, and are incorporated herein by reference in their entirety.

Referring again to FIG. 2A, a user interface 222 can include a variety of interfaces, such as one or more buttons 224, a liquid crystal display (LCD) 226, a vibrator 228, an audio transducer (e.g., speaker) 230, backlight, and/or the like. A backlight can be provided, for example, to aid the user in reading the LCD in low light conditions. The components that comprise the user interface 222 provide controls to interact with the user (e.g., the host). One or more buttons 224 can allow, for example, toggle, menu selection, option selection, status selection, yes/no response to on-screen questions, a "turn off" function (e.g., for an alarm), a "snooze" function (e.g., for an alarm), a reset, and/or the like. The LCD 226 can be provided, for example, to provide the user with visual data output. The audio transducer 230 (e.g., speaker) provides audible signals in response to triggering of certain alerts, such as present and/or predicted hyper- and hypoglycemic conditions. In some embodiments, audible signals are differentiated by tone, volume, duty cycle, pattern, duration, and/or the like. In some embodiments, the audible signal is configured to be silenced (e.g., snoozed or turned off) by pressing one or more buttons 224 on the sensor electronics module and/or by signaling the sensor electronics module using a button or selection on a display device (e.g., key fob, cell phone, and/or the like).

A telemetry module 232 is operably connected to the processor module 214 and provides the hardware, firmware, and/or software that enable wireless communication between the sensor electronics module 12 and one or more display devices. A variety of wireless communication technologies that can be implemented in the telemetry module 232 include radio frequency (RF), infrared (IR), Bluetooth, spread spectrum communication, frequency hopping communication, ZigBee, IEEE 802.11/802.16, wireless (e.g., cellular) telecommunication, paging network communication, magnetic induction, satellite data communication, GPRS, ANT, and/or the like. In one preferred embodiment, the telemetry module comprises a Bluetooth chip. In some embodiments, Bluetooth technology is implemented in a combination of the telemetry module 232 and the processor module 214.

A battery 234 is operatively connected to the processor module 214 (and possibly other components of the sensor electronics module 12) and provides the necessary power for the sensor electronics module 12. In some embodiments, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments the battery is rechargeable. In some embodiments, a plurality of batteries can be used to power the system. In yet other embodiments, the receiver can be transcutaneously powered via an inductive coupling, for example.

A battery charger and/or regulator 236 may be configured to receive energy from an internal and/or external charger. In some embodiments, a battery regulator (or balancer) 236 regulates the recharging process by bleeding off excess charge current to allow all cells or batteries in the sensor electronics module to be fully charged without overcharging other cells or batteries. In some embodiments, the battery 234 (or batteries) is configured to be charged via an inductive and/or wireless charging pad. One skilled in the art appreciates a variety of known methods of charging batteries, which can be implemented with the system described herein, including wired (cable/plug) and wireless methods.

One or more communication ports 238, also referred to as external connector(s), can be provided to allow communication with other devices, for example a PC communication (com) port can be provided to enable communication with systems that are separate from, or integral with, the sensor electronics module. The communication port, for example, may comprise a serial (e.g., universal serial bus or "USB") communication port, allows for communicating with another computer system (e.g., PC, smart mobile phone, personal digital assistant or "PDA," server, or the like). In one exemplary embodiment, the sensor electronics module 12 is able to transmit historical data to a separate computing device for retrospective analysis by a patient and/or physician.

In conventional continuous analyte sensor systems, the on-skin portion of the sensor electronics is generally simplified to minimize complexity and/or size of on-skin electronics, for example, providing only raw, calibrated, and/or filtered data to a secondary display device configured to run calibration and other algorithms required for displaying the sensor data. In contrast, the sensor electronics module 12 executes prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like, which are described in more detail in U.S. Pat. Nos. 7,310,544, 6,931,327, U.S. Patent Publication No. US-2005-0043598-A1, U.S. Patent Publication No. US-2007-0032706-A1, U.S. Patent Publication No. US-2007-0016381-A1, U.S. Patent Publication No. US-2008-0033254-A1, U.S. Patent Publication No. US-2005-0203360-A1, U.S. Patent Publication No. US-2005-0154271-A1, U.S. Patent Publication No. US-2005-0192557-A1, U.S. Patent Publication No. US-2006-0222566-A1, U.S. Patent Publication No. US-2007-0203966-A1 and U.S. Patent Publication No. US-2007-0208245-A1, each of which is incorporated herein by reference in its entirety. Furthermore, the sensor electronics module 12 is configured to store the transformed sensor data (e.g., values, trend information) and to communicate the displayable sensor information to a plurality of different display devices. In some embodiments, the display devices are "dummy" devices, namely, they are configured to display the displayable sensor information as received from the sensor electronics module 12, without any additional sensor data processing.

Figure 2B:
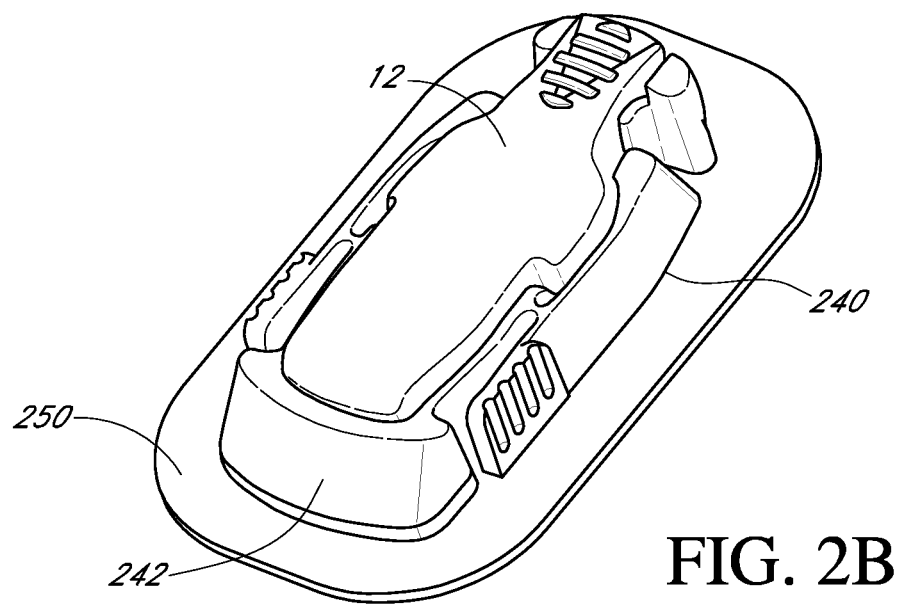
FIG. 2B is a perspective view of the sensor electronics module of FIG. 2A held in a mounting unit in accordance with some embodiments.
Figure 2C:
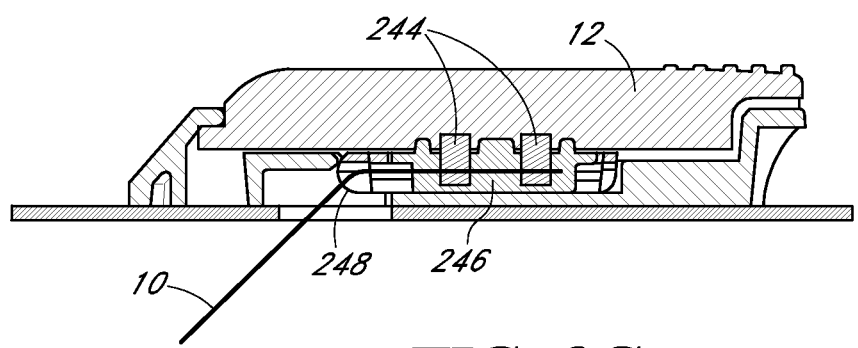
FIG. 2C is a side cross-sectional view of the sensor electronics module and mounting unit of FIG. 2B in accordance with some embodiments.

FIGS. 2B and 2C are perspective and side views of a sensor system including a mounting unit 240 and sensor electronics module 12 attached thereto in some embodiments, shown in its functional position, including a mounting unit and a sensor electronics module matingly engaged therein. In some preferred embodiments, the mounting unit 240, also referred to as a housing or sensor pod, comprises a base 242 adapted for fastening to a host's skin. The base 242 can be formed from a variety of hard or soft materials, and preferably comprises a low profile for minimizing protrusion of the device from the host during use. In some embodiments, the base 242 is formed at least partially from a flexible material, which is believed to provide numerous advantages over conventional transcutaneous sensors, which, unfortunately, can suffer from motion-related artifacts associated with the host's movement when the host is using the device. The mounting unit 240 and/or sensor electronics module 12 can be located over the sensor insertion site to protect the site and/or provide a minimal footprint (utilization of surface area of the host's skin).

In some embodiments, a detachable connection between the mounting unit 240 and sensor electronics module 12 is provided, which enables improved manufacturability, namely, the relatively inexpensive mounting unit 240 can be disposed of when replacing the sensor system after its usable life, while the relatively more expensive sensor electronics module 12 can be reusable with multiple sensor systems. In some preferred embodiments, the sensor electronics module 12 is configured with signal processing (programming), for example, configured to filter, calibrate and/or other algorithms useful for calibration and/or display of sensor information. However, an integral (non-detachable) sensor electronics module can be configured.

In some embodiments, the contacts 244 are mounted on or in a subassembly hereinafter referred to as a contact subassembly 246 configured to fit within the base 242 of the mounting unit 240 and a hinge 248 that allows the contact subassembly 246 to pivot between a first position (for insertion) and a second position (for use) relative to the mounting unit 240. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs. In some embodiments, the contacts 244 are formed from a conductive elastomeric material, such as a carbon black elastomer, through which the sensor 10 extends.

In certain embodiments, the mounting unit 240 is provided with an adhesive pad 250, disposed on the mounting unit's back surface and including a releasable backing layer. Thus, removing the backing layer and pressing the base portion 242 of the mounting unit 240 onto the host's skin adheres the mounting unit to the host's skin. Additionally or alternatively, an adhesive pad 240 can be placed over some or all of the sensor system 8 after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin). The embodiments described with reference to FIGS. 2B and 2C are described in more detail with reference to U.S. Pat. No. 7,310,544, which is incorporated herein by reference in its entirety. Preferably, configurations and arrangements that provide water resistant, waterproof, and/or hermetically sealed properties are provided associated with the mounting unit/sensor electronics module embodiments described herein.

Communication between Sensor System and Display Devices

Figure 3:
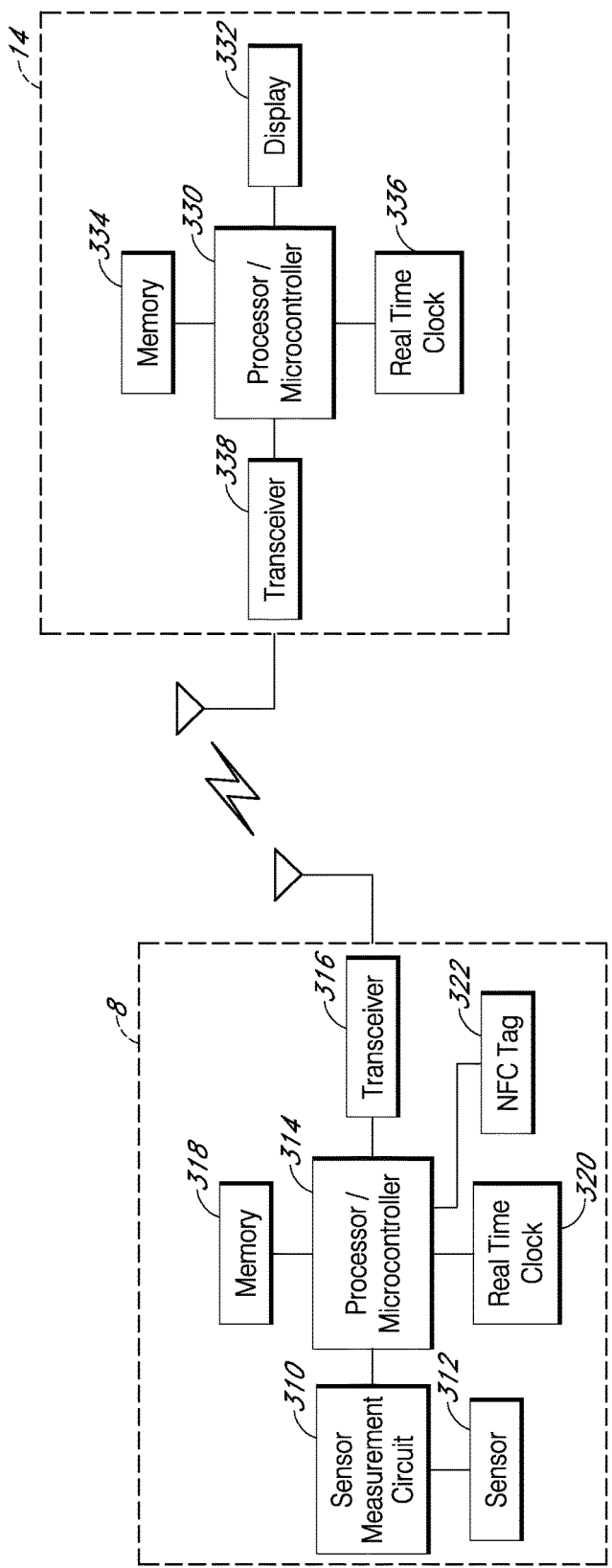
FIG. 3 is an exemplary block diagram illustrating various elements of some embodiments of a continuous analyte sensor system and display device.

FIG. 3 is an exemplary block diagram illustrating various elements of some embodiments of a continuous analyte sensor system 8 in communication with display device(s) 14. The sensor system 8 may include a sensor 312 (also designated 10 in FIG. 1) coupled to a sensor measurement circuit 310 for processing and managing sensor data. The sensor measurement circuit 310 may be coupled to a processor 314 (also designated 214 in FIG. 2A). In some embodiments, the processor 314 may perform part or all of the functions of the sensor measurement circuit 310 for obtaining and processing sensor measurement values from the sensor 312. The processor may be further coupled to a transceiver 316 (e.g., part of item 12 in FIG. 1) for sending sensor data and receiving requests and commands from an external device, such as the display device 14, which is used to display or otherwise provide the sensor data to a user. The sensor system 8 may further include a memory 318 (also designated 220 in FIG. 2A) and a real time clock 320 (part of item 12 in FIG. 1) for storing and tracking sensor data.

Wireless communication protocols may be used to transmit and receive data between the sensor system 8 and the display device 14. The wireless protocol used may be designed for use in a wireless sensor network that is optimized for periodic and small data transmissions (that may be transmitted at low rates if necessary) to and from multiple devices in a close range (e.g., a personal area network (PAN)). For example, the protocol may be optimized for periodic data transfers where transceivers may be configured to transmit data for short intervals and then enter low power modes for long intervals. The protocol may have low overhead requirements both for normal data transmissions and for initially setting up communication channels (e.g., by reducing header overhead) to reduce power consumption. In some embodiments, burst broadcasting schemes (e.g., one way communication) may be used. This may eliminate overhead required for acknowledgement signals and allow for periodic transmissions that consume little power.

The protocol may further be configured to establish communication channels with multiple devices while implementing interference avoidance schemes. In some embodiments, the protocol may make use of adaptive isochronous network topologies that define various time slots and frequency bands for communication with several devices. The protocol may thus modify transmission windows and frequencies in response to interference and to support communication with multiple devices. Accordingly, the wireless protocol may use time and frequency division multiplexing (TDMA) based schemes. The wireless protocol may also employ direct sequence spread spectrum (DSSS) and frequency-hopping spread spectrum schemes. Various network topologies may be used to support low power wireless communication such as peer-to-peer, start, tree, or mesh network topologies. The wireless protocol may operate in various frequency bands such as an open ISM band such as 2.4 GHz. Furthermore, to reduce power usage, the wireless protocol may adaptively configure data rates according to power consumption.

The display device 14 may be used for alerting and providing sensor information to a user, and may include a processor 330 for processing and managing sensor data. The display device 14 may include a display 332, a memory 334, and a real time clock 336 for displaying, storing and tracking sensor data respectively. The display device 14 may further include a transceiver 338 for receiving sensor data and for sending requests, instructions, and data to the sensor system 8. The transceiver 338 may further employ a communication protocol.

In some embodiments, when a standardized communication protocol is used, commercially available transceiver circuits may be utilized that incorporate processing circuitry to handle low level data communication functions such as the management of data encoding, transmission frequencies, handshake protocols, and the like. In these embodiments, the processor 314, 330 does not need to manage these activities, but rather provides desired data values for transmission, and manages high level functions such as power up or down, set a rate at which messages are transmitted, and the like. Instructions and data values for performing these high level functions can be provided to the transceiver circuits via a data bus and transfer protocol established by the manufacturer of the transceiver circuit 316.

Components of the analyte sensor system 8 may require replacement periodically. For example, the analyte sensor system 8 may include an implantable sensor 312 that may be attached to a sensor electronics module that includes the sensor measurement circuit 310, the processor 314, memory 318, and transceiver 316, and battery (not shown). The sensor 312 may require periodic replacement (e.g., every 7-30 days). The sensor electronics module may be configured to be powered and active for much longer than the sensor 312 (e.g., for three, six or more months) until the battery needs replacement. Replacing these components may be difficult and require the assistance of trained personnel. Reducing the need to replace such components, particularly the battery, significantly improves the convenience of the analyte sensor system 8 to the user. In some embodiments, the sensor session as defined above may correspond to the life of the sensor 312 (e.g., 7-30 days). When a sensor electronic module is used for the first time (or reactivated once a battery has been replaced in some cases), it may be connected to a sensor 312 and a sensor session may be established. As will be further described below, there may be a process for initially establishing communication between a display device 14 and the sensor electronics module when it is first used or re-activated (e.g., the battery is replaced). Once the display device 14 and sensor electronics module have established communication, the display device 14 and sensor electronics module may periodically and/or continuously be in communication over the life of several sensors 312 until, for example, the battery needs to be replaced. Each time a sensor 312 is replaced, a new sensor session may be established. The new sensor session may be initiated through a process completed using a display device 14 and the process may be triggered by notifications of a new sensor via the communication between the sensor electronics module and the display device 14 that may be persistent across sensor sessions.

The analyte sensor system 8 gathers analyte data from the sensor 312 that it periodically sends to the display device 14. Data points are gathered and transmitted over the life of the sensor (e.g., 1, 3, 7, 10, 15, 30 or more days). New measurements may need to be transmitted often enough to adequately monitor glucose levels. Rather than having the transmission and receiving circuitry of each of the sensor system 8 and display device 14 continuously communicating, the analyte sensor system 8 and display device 14 may regularly and periodically establish a communication channel between them. Thus, sensor system 8 can communicate via wireless transmission with display device 14 at predetermined time intervals. The duration of the predetermined time interval can be selected to be long enough so that the sensor system 8 does not consume too much power by transmitting data more frequently than needed, yet frequent enough to provide substantially real-time sensor information (e.g., measured glucose values) to the display device 14 for output (e.g., display) to a user. While the predetermined time interval is every five minutes in some embodiments, it is appreciated that this time interval can be varied to be any desired length of time. These predetermined time intervals and associated communications are discussed in more detail with respect to FIG. 9, below.

It should be appreciated that sensor system 8 performs a number of tasks, each of which consume a fair amount of power. Over the life of sensor system 8, power consumption may serve as one of the biggest limitations to completing more and more complex tasks, such as increased data transfer and updates to display device 14. Furthermore, should it be desirable to further decrease the size of sensor system 8, the size of the battery may also need to be reduced, likely resulting in also reducing the life of sensor system 8. Consequently, systems and methods for achieving power savings in conjunction with sensor system 8 are highly desirable.

Low Power Measurement Circuit and Sleep Current Detection

Some embodiments of sensor system 8 may utilize a low power measurement circuit that is capable of switching between a measurement mode and a low power mode to conserve power usage. During the measurement mode, measurement circuitry can be powered and electrically coupled to sensor electrodes to take sensor measurements. Also during the measurement mode, a charging circuit can be powered and electrically coupled to a capacitive circuit to charge the capacitive circuit. After a measurement is complete, the circuit can enter the low power mode. In the low power mode, the measurement circuitry can be decoupled from the sensor electrodes and powered down, and the charging circuitry can be decoupled from the capacitive circuit and powered down. In addition, during the low power mode, the capacitive circuit can be electrically coupled to the sensor electrode or sensor electrodes to maintain a voltage across the electrode(s). In this way, measurement circuitry can be powered down in between taking measurements to reduce power consumption, but yet a voltage can be maintained across the sensor electrodes through the use of capacitive circuit. Maintaining a voltage across the sensor electrodes while measurement circuitry is powered down may be desired. Example low power measurement circuits are described in U.S. Patent Publication No. 20120078071, incorporated herein by reference in its entirety.

In addition to using low power measurement circuitry, circuitry that detects any extra current flowing within sensor system 8 may be useful in ensuring that system 8 is operating efficiently. For example, measuring any excess current flowing within the sensor system 8 when it is in a low power or sleep mode would be desirable. However, to have a measurement means being actively powered to measure the excess current while the system 8 is in sleep mode could be counterproductive, depending upon the implementation, as it could consume power to monitor possible excess current. Furthermore, sending information related to the excess current while the system 8 is in sleep mode may cause the system 8 to wake up prematurely, which could also be undesirable.

Thus, a means for monitoring the current when sensor system 8 is in storage or sleep mode that does not need to be actively powered would be desirable in some implementations. Additionally, a measurement means for detecting excess current that does not cause the system 8 to prematurely wake up from sleep mode to receive the measurement information would be desirable in some implementations. Such measurement means may be implemented in, for example, a separate circuit for measuring current when system 8 is in sleep mode (hereinafter referred to as "sleep current").

Figure 4A:
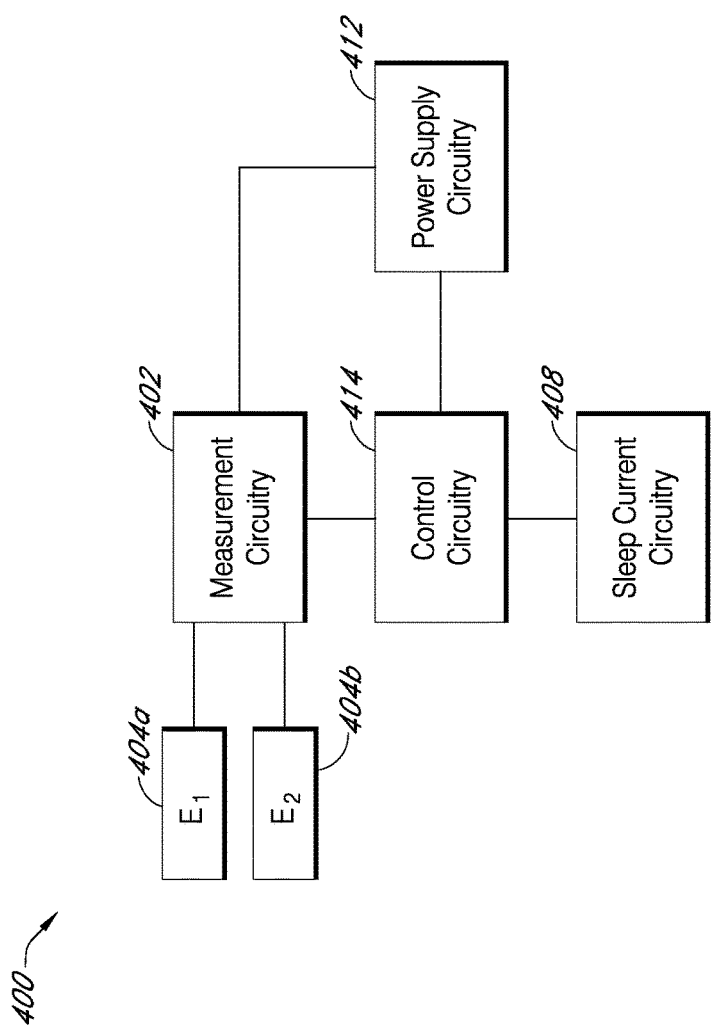
FIG. 4A is a schematic circuit diagram of a low power measurement circuit in accordance with some embodiments.

Reference is now made to FIG. 4A, which is a simplified block diagram of an embodiment of a low power circuit 400 configured to detect sleep current. Low power circuit 400 can include measurement circuitry 402, sensor electrodes 404a and 404b, and sleep current circuitry 408. Also illustrated in FIG. 4A is power supply circuitry 412 and control circuitry 414. Power supply circuitry 412 may be configured to selectively provide power to measurement circuitry 402. In some embodiments, power supply circuitry 412 will not be connected to sleep current circuitry 408, as sleep current circuitry 408 may be configured to operate independently and not require any extra power from circuit 400. Control circuitry 414 may be configured to selectively enable power supply circuitry 412 and selectively enable measurement circuitry 402. Power supply circuitry 412 can include any suitable power supply source, such as a rechargeable, replaceable or disposable battery. Power supply circuitry 412 can also include any other circuitry needed to convert the power source into a suitable voltage source to power the components of circuit 400. Control circuitry 414 can be implemented via an ASIC or a general purpose processor, for example.

Low power circuit 400 can power down measurement circuitry 402 from an active measuring state to a low power inactive sleep state, where the sleep current is measured through the use of sleep current circuitry 408. Control circuitry 414 can be configured to provide a sleep pulse signal to sleep current circuitry 408 when in the inactive sleep state. In some embodiments, the sleep pulse signal is simply a pulse that switches the sleep current circuitry 408 into an on mode, and does not provide any power for an ongoing period of time.

For example, control circuitry 414 may include a timer that places low power circuit 400 in sleep mode for 30 seconds. During this time, a sleep pulse signal (e.g., as a single pulse) flows from control circuitry 414 to sleep current circuitry 408 to switch the sleep current circuitry 408 on. Sleep current circuitry 408 may charge a capacitor, where the voltage across the capacitor correlates with the sleep pulse signal provided to sleep current circuitry 408. After the sleep mode has terminated, an output voltage for the capacitor can be determined by sleep current circuitry 408. This output voltage may be correlated with a characteristic of the sleep pulse signal (e.g., amperes or total charge for the sleep pulse signal) to differentiate any charge in the capacitor resulting from the sleep pulse signal from any sleep current. An error or fault can be identified if the output voltage is above or below pre-determined thresholds. For example, an error message can be displayed to a user if the output voltage is above or below pre-determined thresholds.

Figure 4B:
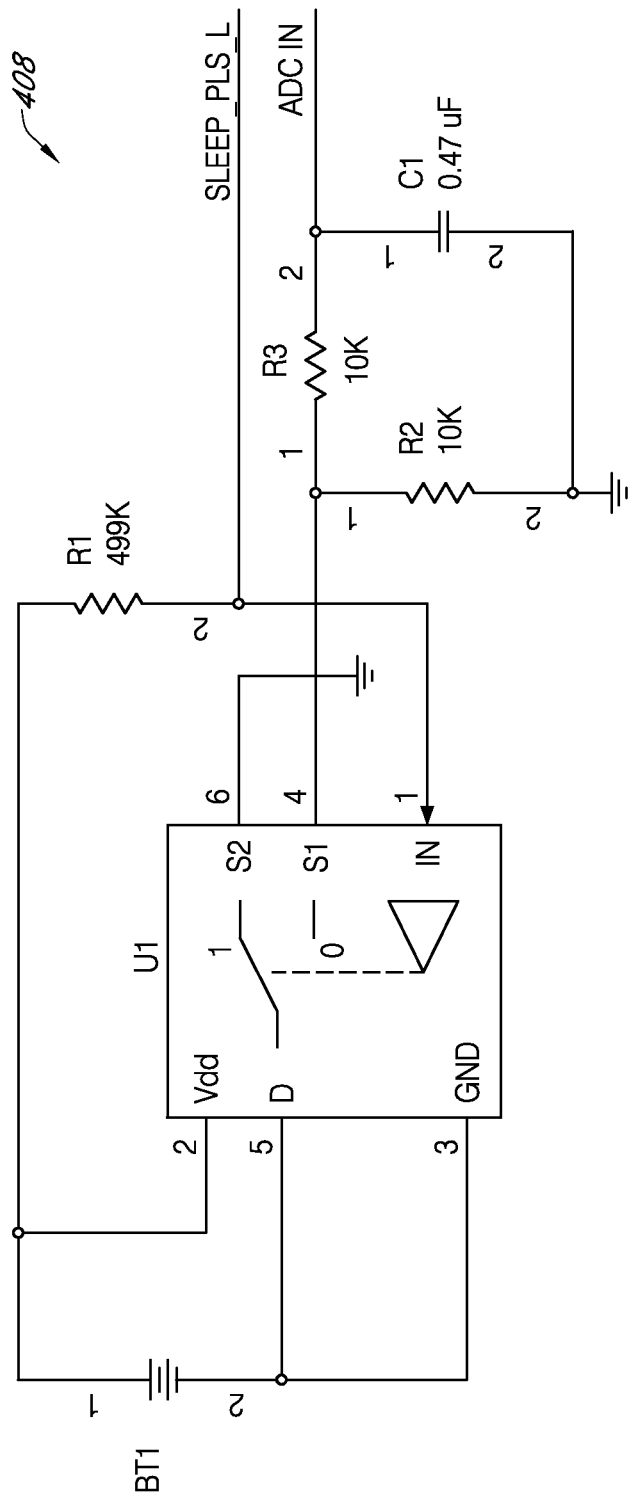
FIG. 4B is a schematic circuit diagram of a sleep current measurement circuit in accordance with some embodiments.

FIG. 4B shows an example of sleep mode circuitry 408 for monitoring current flowing within sensor system 8 when sensor system 8 is in a reduced power or sleep mode. In some embodiments, sleep mode circuitry 408 captures any current resulting from the sleep pulse signal as well as any sleep current as a charge on a capacitor from a large current sense resistor that may be automatically switched out of the circuit by hardware (e.g., internal to a processor) when the system 8 wakes or powers up. The system 8 can then immediately read the charge on the capacitor to determine if the total current reading (e.g., current attributable to sleep pulse signal and the sleep current) is within an acceptable range.

Still referring to FIG. 4B, sleep current circuit 408 may include an analog switch U1 powered by a battery BT1. A first resistor R1 may maintain switch U1 in state S2, connecting battery BT1 to system ground GND. It should be appreciated that, in some embodiments, the sleep pulse signal may simply change the state of sleep current circuit 408 into an active measuring or on mode. The sleep pulse signal may comprise a single pulse, being almost instantaneous and having no lasting duration (e.g., a millisecond or more). Generally, the sleep pulse signal may result in some charge in circuit 408. This resultant charge may be subtracted from the total measured charge to determine the sleep current or taken into account when comparing the total charge to a threshold.

Figure 4C:
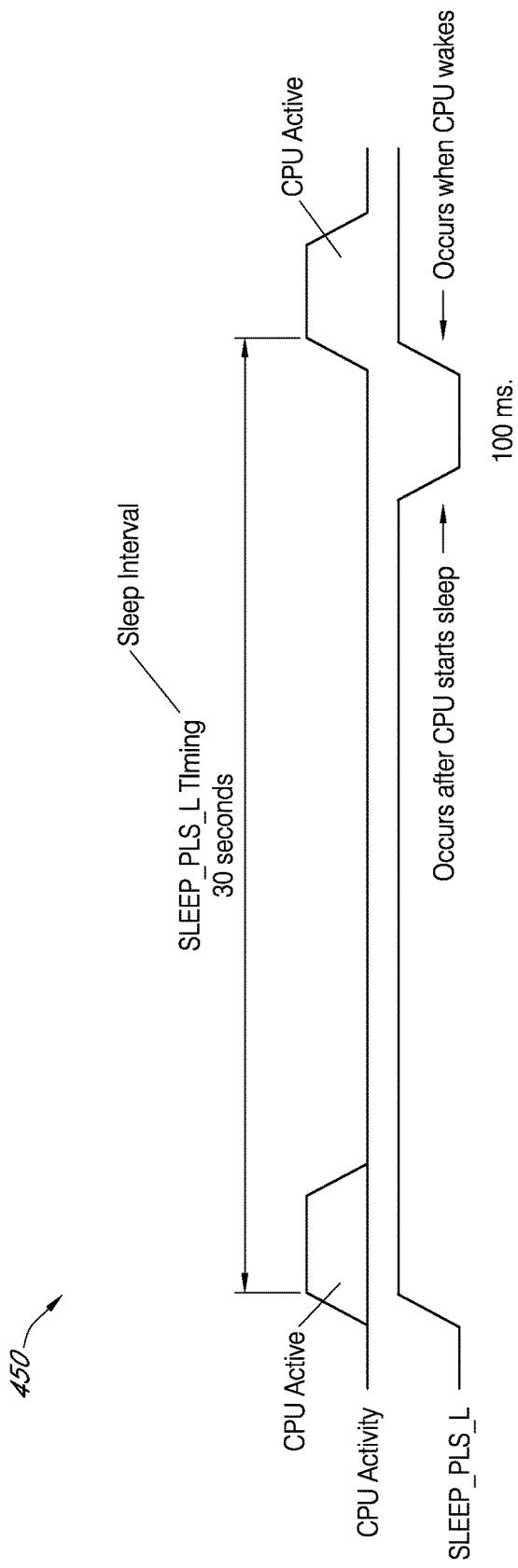
FIG. 4C is a sleep timing graph for the circuit of FIG. 4A in accordance with some embodiments.

FIG. 4C shows a sleep timing diagram 450 with a sleep interval set for 30 seconds. In some embodiments, software may be used to set up a timer that will wake the processor from its sleep mode. The processor is briefly active when entering sleep mode to set the timer (shown in the time series "CPU Active" in FIG. 4C). In some embodiments, a sleep pulse signal is generated (e.g., from a processor) that goes low for a short time (e.g., about 100 ms) before wake up occurs, switching battery BT1 to state S1. The sleep pulse signal is shown in the time series "SLEEP_PLS_L" in FIG. 4C. The processor becomes active again at the end of the 30-second sleep interval.

Referring again to FIG. 4B, at state S1, capacitor C1 has a voltage that correlates to the sleep pulse signal (due to resistor R2). This voltage may be transferred through resistor R2 to capacitor C1. It will be appreciated that the sleep pulse signal is applied long enough to charge capacitor C1 to the level of resistor R2.

When wake up of system 8 occurs, state S2 is re-entered, while preserving the voltage at capacitor C1. In some embodiments, software may use an ADC channel (shown in FIG. 4B as ADC_IN) to read the charge on capacitor C1 before it is discharged through resistors R2 and R3. The charge at capacitor C1 due to the current received from battery BT1 via resistor R1 may be accounted for when correlating the sleep pulse signal with the charge on capacitor C1 (e.g., an amount of charge subtracted due to current from battery BT1).

Because sensor system 8 may spend a substantial amount of time sleeping or in a lower power mode, if the output voltage on the capacitor is higher than expected (e.g., greater than an amount expected from the sleep pulse signal, the internal battery of the sleep current circuit, or combination thereof), battery life may be significantly shortened due to unwanted sleep currents in the system. This present circuit allows sensor system 8 to verify correct operation and normal battery drain when it is sleep mode. If a fault is indicated, diagnostics or remedial action can occur. For example, in some implementations, the sensor system may monitor and record possible technical issues associated with the sensor system 8. The technical issues may be recorder in a technical support log file stored in memory of the sensor system Auto-zero Compensation In some embodiments, an additional verification may be performed on a sensor signal due to possible leakage currents. As used herein, leakage current refers to any current that flows when the ideal current is zero and the system 8 is an active measurement mode (e.g., as opposed to standby, disabled, or "sleep" mode, as described above). These devices can draw one or two microamperes while in their quiescent state compared to hundreds or thousands of milliamperes while in full operation. These leakage currents are becoming a significant factor to portable device manufacturers because of their undesirable effect on e.g., battery run time.

As is known by one of skill in the art, sensor data may comprise digital data in "counts" converted by an A/D converter from an analog signal (e.g., voltage or amps). Leakage current may affect the sensor data reading directly by showing an increase in counts (e.g., a high leakage current will produce an increased value for the converted counts).

In some embodiments, the leakage current may change as a result of the internal temperature of various hardware components (such as illustrated in FIG. 2A) changing. In such embodiments, the leakage current may be determined by: (1) determining if the internal temperature of one or more hardware components has changed, and (2) if the internal temperature of one or more hardware components has changed, measuring the leakage current. For example, in some embodiments, the leakage current may be measured by creating an open circuit at or near the location where leakage is expected. It should be appreciated that any circuit capable of detecting leakage current, as is known by one of skill in the art, may be implemented by the present disclosure.

In some embodiments, a leakage current is detected for sensor system 8 using a leak detection circuit in communication with the sensor system 8. The leakage current may be received by the sensor system (e.g., via a processor). Thereafter, an adjustment may be performed on or more sensor signals using the leakage current. For example, the adjustment to the sensor signal may be subtracting the leakage current from a sensor signal. In other words, the leakage current may be "auto-zeroed" out from the sensor signal. In some embodiments, the adjusted sensor signal may be provided to a user in a desirable format (e.g. as sensor count data).

Low Power Storage Mode

Some embodiments reduce the amount of power consumed by sensor electronics module 12 by putting sensor electronics module in a power saving storage mode while it is in storage. In general, a storage mode can be activated with a command at manufacturing that initiates a routine implemented by software stored in memory, for example, to power off select circuitry in sensor electronics module 12 and put processor module 414 into a low power mode (e.g., sleep mode). Sensor electronics module 12 can then be placed in a package that places sensor electronics module 12 next to a storage magnet, which keeps it in storage mode until sensor electronics module 12 is pulled away from the magnet by a user. The storage magnet can be incorporated into the packaging directly next to where the sensor electronics module 12 is held, for example.

In some embodiments, pulling a magnet away from sensor electronics module switches sensor electronics module 12 out of a storage mode and into a normal operation mode. For example, pulling the sensor electronics module 12 away from the magnet can trigger an interrupt line, which initiates an interrupt routine performed by software stored in the electronics module 12. Once started, the interrupt routine can initiate a state machine implemented using sleep timer interrupts which check periodically across multiple intervals, for a predetermined amount of time, such as five minutes, to validate that the sensor electronics module 12 has indeed been moved away from the magnet. Once the state machine concludes that the storage magnet has been removed, the state machine puts sensor electronics module 12 in normal operation mode by, for example, pulling processor 314 out of low power mode, and restoring or providing power to other circuitry of sensor electronic module 12.

Figure 5A:
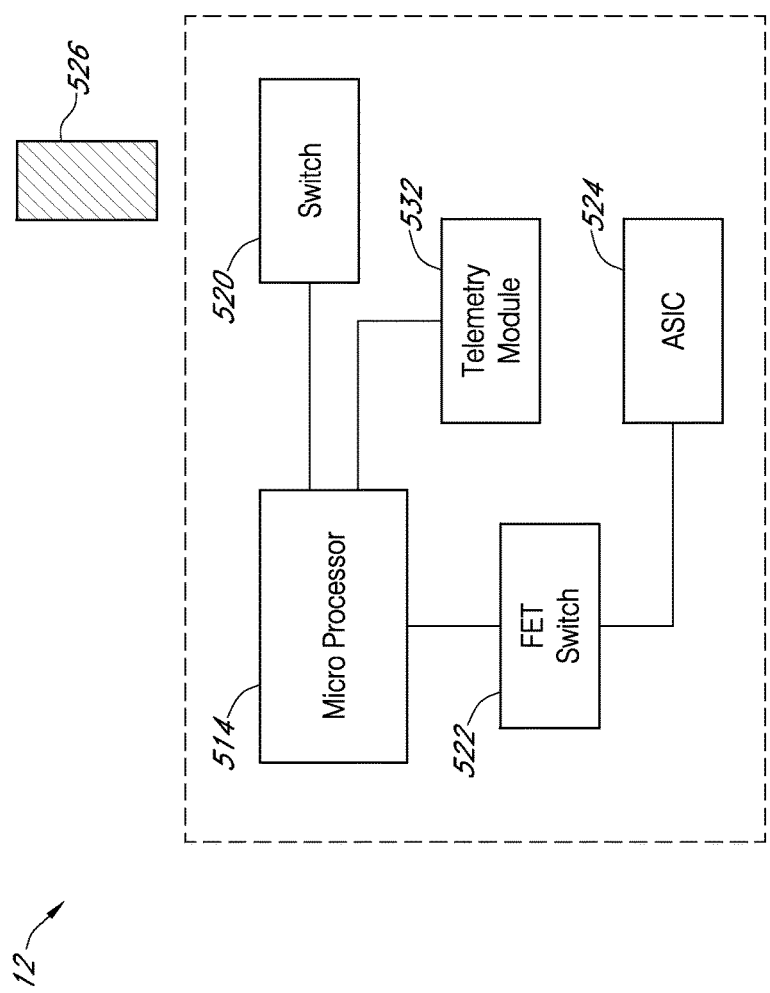
FIG. 5A is a simplified block diagram of an embodiment of sensor electronics module with a low power storage mode feature.

FIG. 5A is a simplified block diagram of an embodiment of sensor electronics module 12 with a low power storage mode feature. For ease of explanation, FIG. 5A only illustrates select components of a sensor electronics module 12 and it is understood that further components can be incorporated into sensor electronics module 12, such as any components discussed above with reference to FIG. 5A. Furthermore, a sensor kit can also be provided that includes one or more sensor electronics modules 12 and a plurality of sensors 10, which include low power mode storage feature(s). Such sensor kits are described in further detail in U.S. Patent Publication No. 20120078071, incorporated herein by reference in its entirety.

As illustrated in the embodiment of FIG. 5A, sensor electronics module 12 includes a switch 520 configured to switch between a first state (e.g., closed state) when a force is applied to the switch and second state (e.g., open state) when the force is removed or sufficiently diminished. In some embodiments, the applied force is a magnetic field, generated by any suitable means (e.g., mechanical or electrical). Switch 520 is operatively connected to system processor 514, which is in turn operatively connected to ASIC 524 via FET switch 522. Telemetry module 532 is also operatively connected to microprocessor 514.

In some embodiments, switch 520 is a reed switch. In other embodiments, switch 520 is a Hall-effect switch. When switch 520 is a reed switch, it includes one or more pairs of magnetizable, flexible, metal reeds whose end portions are separated by a small gap when the switch is open. The reeds may be hermetically sealed in opposite ends of a tubular glass envelope. A magnetic field (from an electromagnet or a permanent magnet) will cause the reeds to come together, thus completing an electrical circuit. Good electrical contact may be assured by plating a thin layer of non-ferrous precious metal such as low-resistivity silver over flat contact portions of the reeds.

When switch 520 is a Hall-effect switch, it includes a transducer that varies its output voltage in response to a magnetic field. For example, in some embodiments, the Hall-effect switch is mounted onto a PCB, similar to other components of FIG. 5A. Hall-effect switch may be triggered by an external magnet, such as magnet 526 described below. In some embodiments, a Hall-effect switch may be preferable to other switch types such as a reed switch, which may be sensitive to vibration and shock and to a light switch, since not optical window is required for the Hall-effect switch.

In some embodiments, the sensor electronics module 12 includes a light-sensitive sensor that triggers the switch between the first state and the second state. That is, the light sensitive-sensor takes the sensor electronics module out of a storage mode when the light-sensitive sensor is exposed to light in accordance with some embodiments. To illustrate, sensor electronics module 12 can be placed in a low power, storage mode during manufacture, shipment and storage so the sensor electronics module consumes little power. A light-sensitive sensor can be included in sensor electronics module 12 that is shielded from light by a protective cover and the sensor electronics module placed in a storage mode in a similar manner as described above. Thus, during manufacture, shipment and storage of sensor electronics module 12, the sensor electronics module can be in the storage mode.

A user can remove the protective cover—thereby exposing the light-sensitive sensor to light—to cause the sensor electronics module to switch from the storage mode to a higher power, operational mode (e.g., when the sensor electronics module 12 needs to be woken up for use).

Figure 5B:
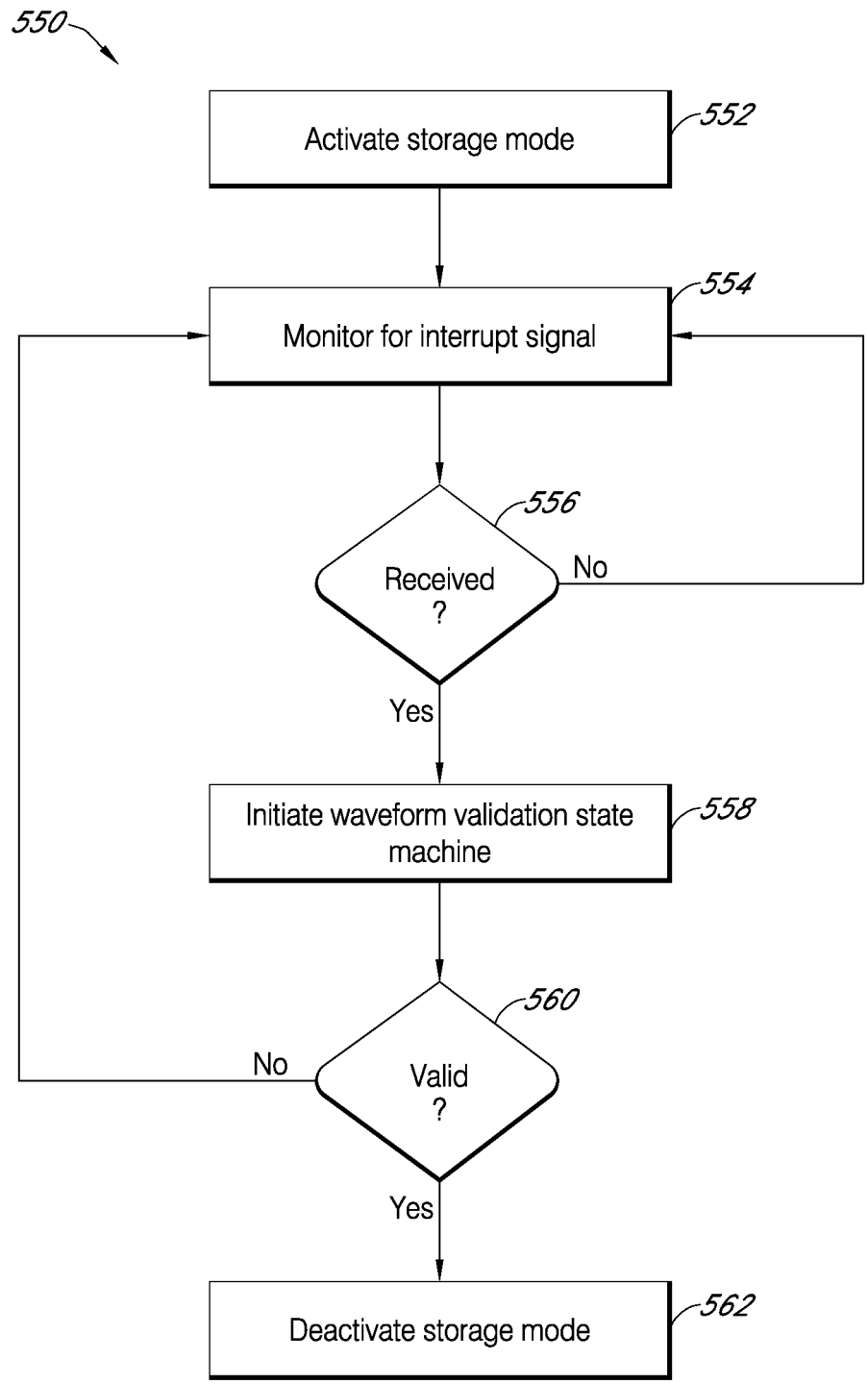
FIG. 5B is a flow chart of an exemplary process for placing sensor electronics module into a storage mode and taking sensor electronics module out of the storage mode.

An exemplary process 550 for placing sensor electronics module 12 into a storage mode and taking sensor electronics module out of the storage mode will now be described with reference to the flowchart depicted in FIG. 5B. It is understood that process 550 is illustrative only, and that additional steps can be added and/or one or more steps of process 550 can be removed. In addition, the steps of process 550 are not limited to the described order.

Process 550 starts with activating a storage mode at block 552. A variety of methods can be used to activate the storage mode. In some embodiments, a storage mode command is transmitted from an external telemetry device and received by sensor electronics module 12 via telemetry module 532. The telemetry module 532 relays the storage mode command to microprocessor 514, which, in response, initiates a storage mode routine. In some embodiments, a storage mode command can be initiated by inputting a command via a user interface, such as user interface 222 of FIG. 2, of a sensor electronics module 12.

Further to block 552, the storage mode routine can include turning off electronic components of sensor electronics module 12 and/or placing electronic components of sensor electronics module 12 in a low power mode (also referred to as a sleep mode). In some embodiments, microprocessor 514 is placed in a low power mode and all other electronic components that need not be used during storage of the sensor electronics module 12, such as a potentiostat 210, and any unneeded circuits are turned off. For example, processor 514 of FIG. 5A can send a switch enable signal via a data line to turn off FET switch 522, which, in turn, turns off ASIC 524.

Also included in block 552, magnet 526 is placed in proximity to switch 520 to cause switch 520 to be in a first state (e.g., a closed state). In some embodiments, switch 520 needs to be in the first state prior to sensor electronics module 12 receiving the storage mode command in order for the storage mode routine to be initiated. In another embodiment, the storage mode interrupt routine is initiated as long as switch 520 is placed in the first state during a predetermined amount of time after the sensor electronics module 12 receives the storage mode command.

In some embodiments, the sensor electronics module 12 is checked to make sure it entered storage mode after the transmitting the storage mode command. This can be accomplished by placing the sensor electronics module 12 in a radio transmission detection device that monitors radio frequencies being emitted from the sensor electronics module. Because the sensor electronics module 12 automatically sends periodic radio frequency transmissions (e.g. every five minutes) in some embodiments, as discussed above, the radio transmission detection device will detect radio transmission from the sensor electronics module should the sensor electronics module not be placed in the storage mode and should the radio transmission detection device be monitoring the sensor electronics module for a time period longer than the periodic transmission time interval. By performing this check, the manufacturer can reduce the likelihood that a sensor electronics module 12 is sent to a customer with a depleted battery due to the sensor electronics module not being placed in the storage mode.

Next, at block 554, microprocessor 514, while in a low power mode, monitors for an interrupt signal from switch 526. In some embodiments, an interrupt signal is sent from switch 526 when switched to a second state (e.g., open state), which occurs when magnet 526 is no longer in sufficient proximity to switch 520 to keep switch in the first state. This can occur, for example, when sensor electronics module 12 is removed from storage packaging in which magnet 526 can be embedded.

At decision block 556, process 550 determines whether an interrupt signal has been received. If not, then process 550 returns to block 554 to continue monitoring for an interrupt signal. If it is determined that an interrupt signal has been received, then process 550 proceeds to block 558.

Process 550 may initiate a state machine validation routine at block 558. In some embodiments, the state machine validation routine verifies at predetermined intervals that the switch signal continues for a predetermined amount of time. For example, each predetermined interval can be one minute and the predetermined amount of time can be five minutes. In such an example, processor 514 can be woken each interval (e.g., each minute) to verify that the switch signal continues to be in the inactive state and the processor is placed in a sleep mode in between verification intervals to conserve power. Should microprocessor 514 determine that the switch signal has returned to the activated state—which can occur if magnet 526 is moved to be in sufficient proximity to switch 520 or if a signal glitch occurs, (which can be further mitigated using a debounce or second check to make sure the signal was not glitched), for example—then the validation routine ends and it is determined that the removed magnet state is not valid. In some embodiments, a signal glitch may be the result of stray magnetic fields. However, the removed magnet state is considered valid if, after the expiration of the predetermined amount of time, microprocessor 514 has seen the correct switch signal level at each verification interval.

Next, decision block 560 queries whether the removed magnet state is valid. If not valid, then process returns to block 554. However, if valid, then process proceeds to block 562.

At block 562, process 550 deactivates the storage mode. Here, components of sensor electronics module 12 are switched into a normal operation mode. For example, microprocessor can be woken out of a sleep mode and turn on FET switch 522, which, in turn, enables ASIC 524 and any other components of sensor electronics module 12 that are used during a normal operation mode.

In some embodiments, process 550 can be performed not only when the sensor electronics module 12 is placed in storage, but also after sensor electronics module 12 is initially removed from its packaging. In this way, a user can place the sensor electronics module in a low power mode whenever desired; for example, when on an airplane or any other time it is determined that the sensor electronics module 12 should not or need not be powered. In this regard, some embodiments provide a magnetic clip (not shown) that is configured to hold magnet 526 in proximity to switch 520. A user can then attach the magnetic clip to sensor electronics module 12 and initiate a storage mode command to begin process 550.

In some embodiments, sensor electronics module 12 can be configured to prevent re-entry of the storage mode once taken out of the storage mode. This may be beneficial to prevent the sensor electronics module 12 from accidentally re-entering storage mode during use, among other reasons. Sensor electronics module 12 can be configured to prevent storage mode after the sensor electronics module 12 is taken out of storage mode by disabling switch 420 or the data line connecting switch 520 to processor 514, for example.

In some embodiments, a process is used to prevent or reduce the likelihood of inadvertent reentry into storage mode. For example, in one implementation, a simple transition on the switch 520 is not sufficient to put the transceiver 316 (e.g., of sensor electronics module 12) back in storage mode. In some embodiments, a specific complex magnetic pulse waveform is required in order to put the sensor electronics module 12 into a test mode in which the sensor electronics module is configured to be able to receive a storage mode command over an RF interface. In addition, the storage mode command can be unique for each sensor electronics module 12 and can be required to be received within a predetermined amount of time (e.g., 10 seconds) of the sensor electronics module 12 successfully entering the test mode. If any of these conditions are not met, the sensor electronics module 12 does not return to storage mode.

Automatically Switching on Sensor Electronics

With reference to FIG. 1, some embodiments of a system for continuous measurement of an analyte automatically switch a sensor electronics module 12 from a low power mode (e.g., power off mode or low power storage mode) to a higher power operational mode when the sensor electronics module is attached to a disposable sensor, such as continuous analyte sensor 10 and/or mounting unit 240. Doing so can reduce power consumption during the shelf-life of the sensor electronics module 12 as well as in between sensor attachments. As described above with respect to FIGS. 2B and 2C, some embodiments of sensor system 8 can use sensor electronics module 12 that is configured to be releasably attached to mounting unit 240, wherein the mounting unit holds sensor 10 when the sensor is implanted in a host.

In some embodiments, a connector pad of sensor electronics module 12, configured to contact corresponding contact(s) of mounting unit 240, can be split into two individual, electrically insulated connectors. The contact(s) of the mounting unit 240 can be in the form of a conductive, flexible "puck", designed to make contact with the corresponding "split" connector of the sensor electronics module when sensor electronics module is attached to the mounting unit. Once in contact, the split connector and the conductive puck result in a short circuit. This can cause sensor electronics module to switch on after an impedance measurement or switch on a battery voltage to wake up the sensor electronics module.

Figure 7:
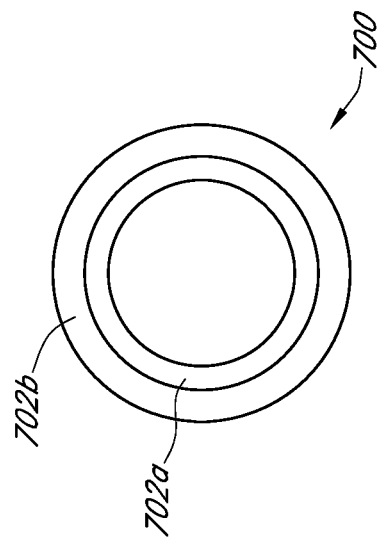
FIG. 7 illustrates an embodiment of a split connector having a concentric layout in accordance with some embodiments.
Figure 6:
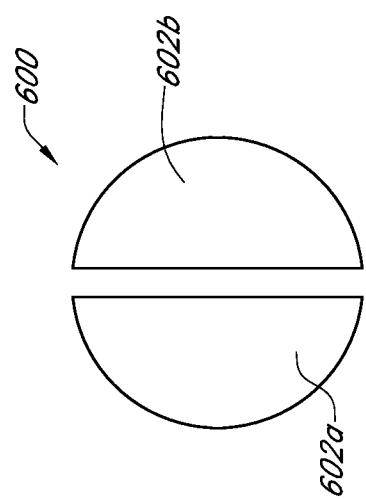
FIG. 6 illustrates an embodiment of a split connector having an axial symmetric layout in accordance with some embodiments.

FIGS. 6 and 7 are top views of respective embodiments of split connectors 600, 700 of sensor electronics module 12. FIG. 6 illustrates an embodiment of a split connector 600 having an axial symmetric layout, where connector 600 is split into two semicircular partial contacts 602a and 602b. FIG. 7 is an embodiment of a split connector 700 having a concentric (co-axial) design, where a first partial contact 702a is encircled by a second partial contact 702b. A space is provided between contacts 702a and 702b to insulate the contacts from one another.

Figure 8:
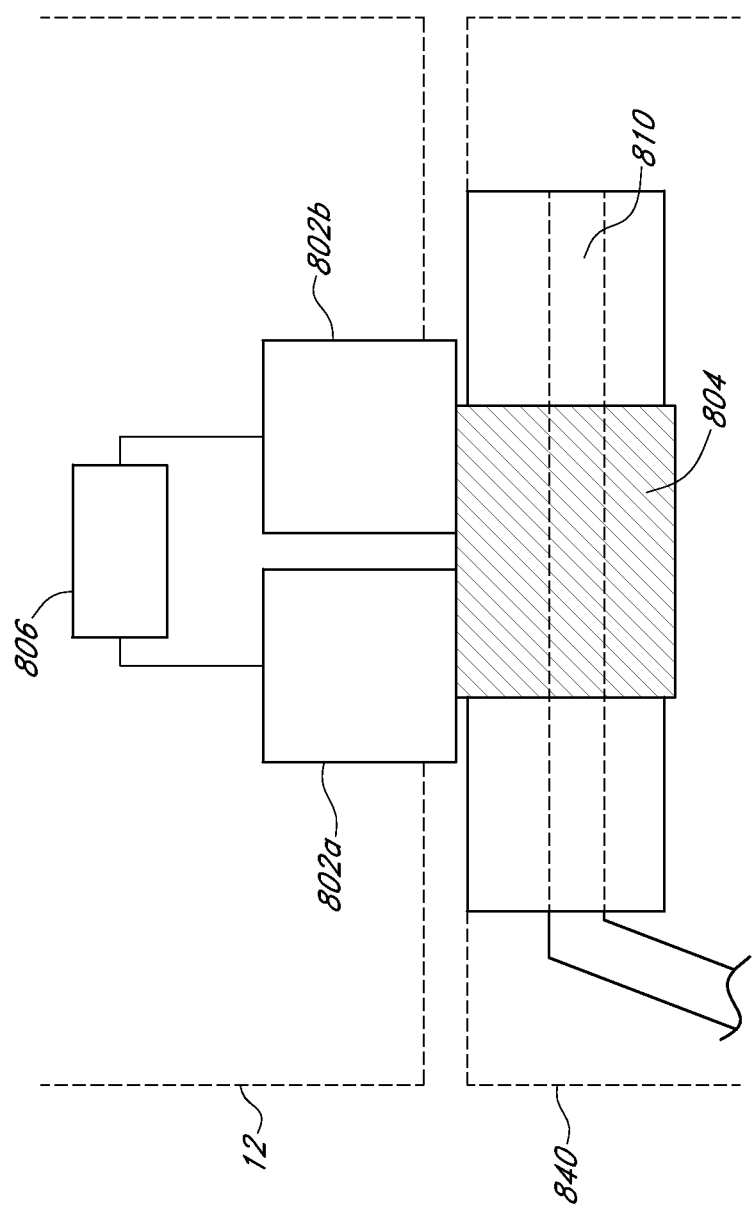
FIG. 8 is a schematic cross-sectional view of a sensor electronics module attached to a mounting unit in accordance with some embodiments.

FIG. 8 illustrates a partial cross-sectional view of a sensor electronics module attached to a mounting unit in accordance with some embodiments. Here, sensor electronics module 12 is attached to mounting base 840, which can include any of the features of mounting base 240 described herein. When attached, both partial contacts 802a and 802b of sensor electronics module 12 make contact with conductive sensor puck 804 of mounting unit 840. Partial contacts 802a and 802b can be partial contacts 802a and 802b, respectively, or partial contacts 702a and 702b, respectively, discussed above. The contact allows for switching on sensor electronics module 12 as well as providing connection of a potentiostat (not shown in FIG. 8) in the sensor electronics module with sensor 810.

The embodiment of FIG. 8 uses electronic switch 806 based on a measurement of impedance (resistance) between contacts 802a and 802b. Without sensor puck 804 in contact with partial contacts 802a and 802b, the impedance measurement should be, theoretically, infinitely high. When sensor electronics module 12 is attached to sensor unit 820, conductive puck 804 shorts the two contacts 802a and 802b, which results in a measurable, low resistance. This resistance can be measured by a simple circuit incorporated in switch 806. The circuit can draw minimum or no power. Upon measuring the low resistance, switch 806 can switch power up the electronics module 12 from a low power state.

The switch 806 can connect and disconnect a battery circuit to cause sensor electronics module 12 to switch between a low power state and a high power state. The battery circuit can be separate from or incorporated in the sensor electronics module 12. Further, when connected, the battery circuit can power some or all the components of the sensor electronics module in some embodiments. For example, in some embodiments a first battery circuit connected to the switch 806 provides power to some, but not all, components of the sensor electronics module, such as components used to drive the sensor during a measurement cycle, when connected, and a separate, second battery circuit provides power to components of the sensor electronics module regardless of whether the first battery circuit is connected via the switch. The first and second battery circuits can be powered by the same or different batteries.

When switch 806 is connected to a battery circuit, connection of the mounting base 840 to sensor electronics module 12 causes switch 806 to close the battery circuit, which powers up the sensor electronics module. Further, disconnecting the sensor unit 820 from the sensor electronics module 12 causes switch to open the battery circuit, which powers down the sensor electronics module.

In addition to or instead of one or more connector pads of sensor electronics module 12, an electrode probe that determines if sensor electronic module 12 is connected to a sensor 10. For example, in some embodiments, an electrode probe e.g., part of or in communication with a sensor electronic module 12, may send a signal e.g., every five minutes to determine if sensor electronic module 12 is connected to sensor 10. In some embodiments the probe conducts periodic checking for the connection between the sensor electronics module 12 and sensor 10. The probe signal may be selected from electrical (e.g. resistance), mechanical, etc. signals.

Sensor Initialization and Communication

Once sensor electronics module 12 has been switched from a low power mode (e.g., power off mode or low power storage mode) to a higher power operational mode (e.g., when the sensor electronics module 12 is first attached to a disposable sensor 10), a sensor initialization process begins in accordance with some embodiments. Accordingly, each time a new sensor 10 is connected to the sensor electronics module 10, an initialization process may occur in accordance with some embodiments.

For example, when a sensor is first inserted into a host, there is a time when the sensor may need to equilibrate or stabilize (e.g., the sensor may hydrate or swell, tissue damage and an immune response may result from insertion of the sensor, etc.), as is known to those of skill in the art. Furthermore, during this equilibration time period, the sensor may not provide accurate measurements because the bias voltage when first applied needs to come up to a stable value. Consequently, in some situations it can be desirable to wait an amount of time after insertion of the sensor to allow the sensor to equilibrate in vivo. In some embodiments, the sensor electronics can perform an initialization process aid in stabilizing the sensor. A non-limiting example includes applying a voltage that is higher than the normal bias voltage to the sensor.

Use of Data Communication Protocols

Figure 9A:
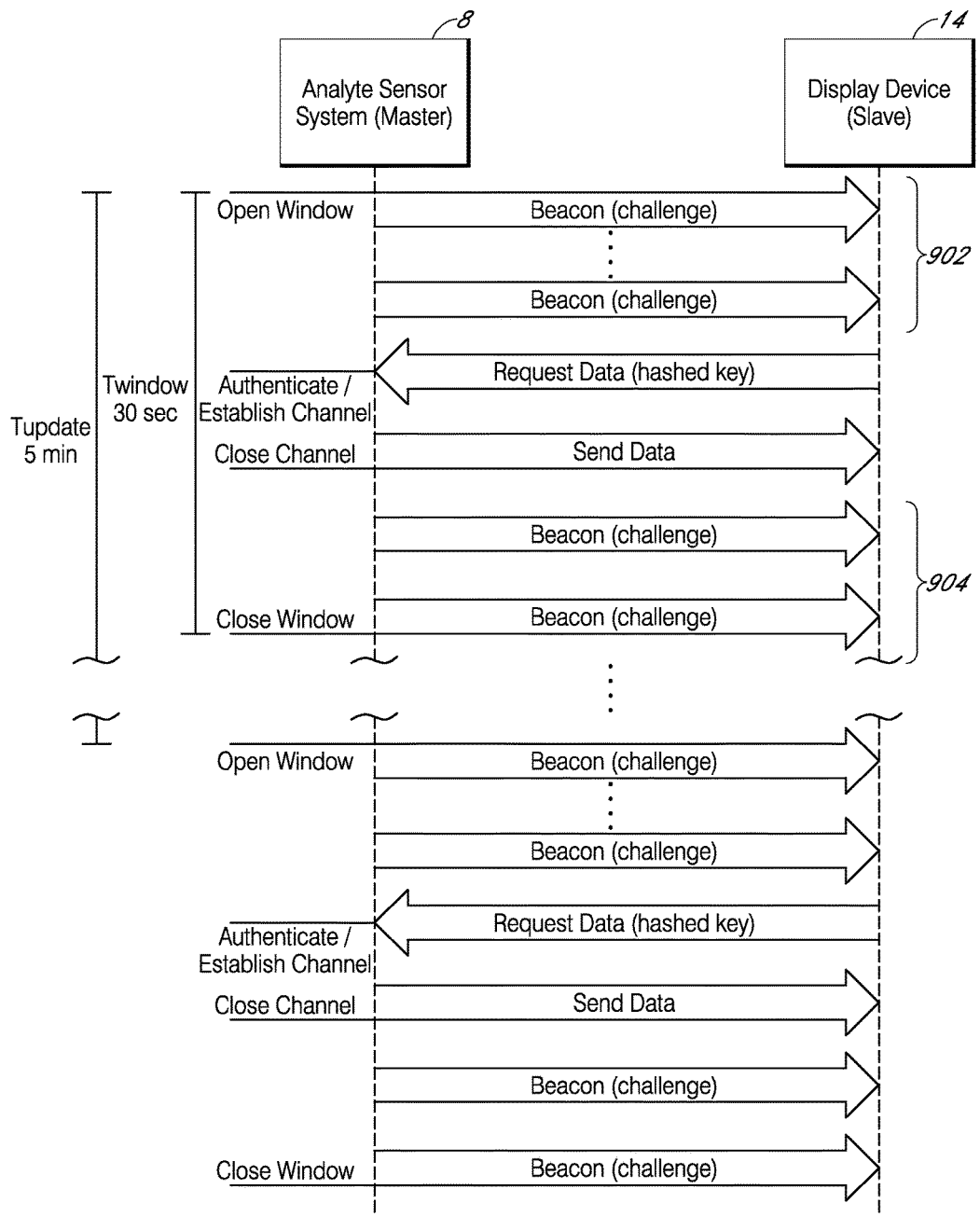
FIG. 9A is a flow diagram of an exemplary communication between an analyte sensor system and a display device for communicating glucose measurement values.

FIG. 9A is a flow diagram of an exemplary communication between an analyte sensor system 8 and a display device 14 for communicating glucose measurement values. The data transfer may happen periodically, at times separated by an update interval $T_{update}$ that may correspond to a period of obtaining and sending a recently measured glucose value (e.g., five minutes). In between these data transfer procedures, the transceiver 316 of the analyte sensor system 8 can be powered down or in a sleep mode to conserve battery life. As such, the analyte sensor system 8 may therefore establish a communication channel with the display device 14 once per update interval $T_{update}$. Establishing a communication channel may occur during a transmission window $T_{window}$ within an update interval $T_{update}$.

To establish a communication channel, the analyte sensor system 8 may send one or more message beacons during of a transmission window $T_{window}$ within an update interval $T_{update}$. Each message beacon may be considered an invitation for a display device 14 to establish a communication channel with the sensor system 8. A beacon may include data including a challenge value for authenticating a display device 14. During initial system set up, the display device 14 may listen continuously until such a message beacon is received. When the beacon is successfully received, the display device 14 can acknowledge the reception to establish communication between the devices. In response to the beacon, the display device 14 may send a message requesting a measurement along with a computed value for authentication. Once authenticated, the analyte sensor system 8 and display device 14 may exchange information to determine how data will be exchanged (e.g., a specific frequency, time slot assignment, etc.). When the desired data communication is complete, the channel can be closed, and the transceiver 316 of the analyte sensor system 8 (and possibly the transceiver 338 of the display device 14 as well) can be powered down. The entire data transmission window interval $T_{window}$ for providing data to one or more display devices 14 may be a small fraction of the update interval $T_{update}$. For example, $T_{update}$ may be five minutes and the data transmission window interval $T_{window}$ may be thirty seconds. As such, the transceiver 316 of the analyte sensor system 8 may only be powered for substantially 30 seconds of a five minute $T_{update}$ interval. This may significantly reduce power consumption. In some cases, the transceiver 316 is not completely powered down, but enters a low-power mode when not transmitting. After a $T_{update}$ interval has elapsed, the transceivers 316, 338 can be synchronized to power up again substantially simultaneously, and establish a new communication channel using the same process to exchange any new data as shown in FIG. 9A. This process may continue, with new communication channels being established at the pre-determined intervals.

To allow for some loss of synchronization between the two devices in between transmissions, the analyte sensor system 8 may be configured to send a series of message beacons 902 in a window of time around the scheduled transmission time (e.g., 8 message beacons per second for 4 seconds). Any one of the message beacons can be used to initiate the establishment of a new communication channel when it is received by the display device 14. After communicating with one device during the transmission window, the analyte sensor system 8 may send out further message bacons 904. These beacons can be received and used to establish other communication channels with other devices (e.g., other display devices) during the transmission window $T_{window}$. However, in some embodiments, if it is known that the analyte sensor system 8 is only communicating with a single display device, then the transmission window $T_{window}$ can be terminated at the same time as closing the communication channel with the display device.

Figure 9B:
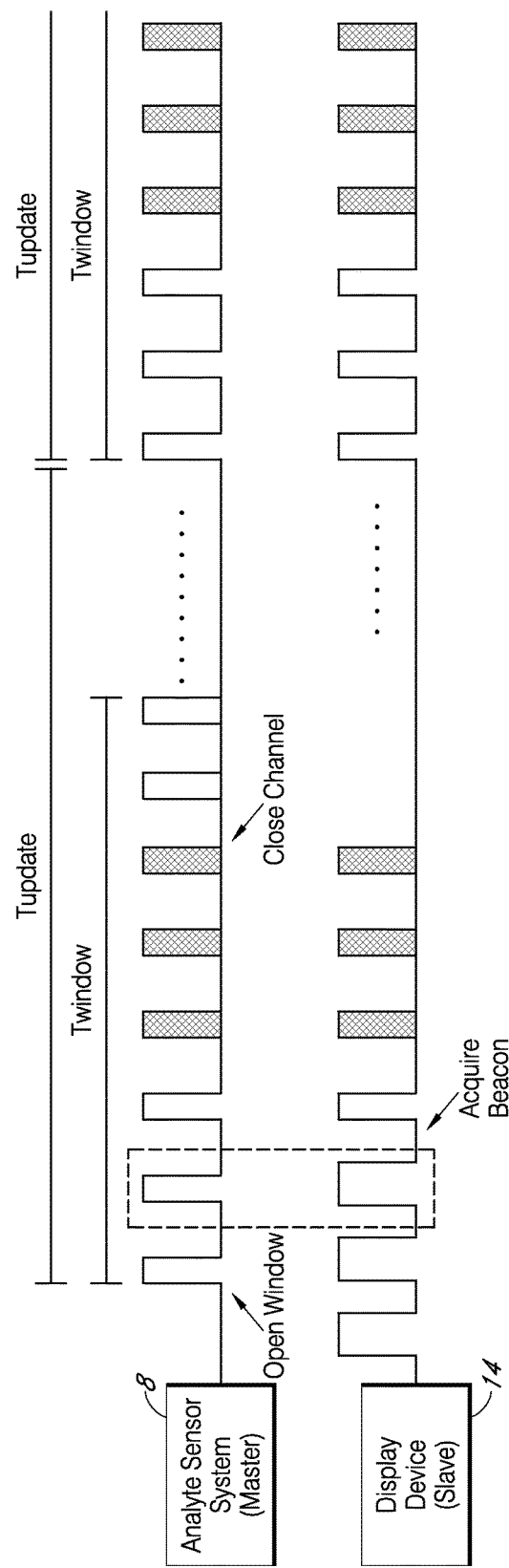
FIG. 9B is a timing diagram of en exemplary sequence for establishing a communication channel between an analyte sensor system and a display device.

FIG. 9B is a timing diagram of an exemplary sequence for establishing a communication channel between an analyte sensor system 8 and a display device 14. The display device 14 may initially "wake up" its transceiver 316 and wait to receive a beacon from the analyte sensor system 8. Once the analyte sensor system 8 begins sending beacons, it may take one, two, or more beacons for the display device 14 to receive the beacon and respond with a request. Once the beacon is received and the request sent, data may thereafter be sent and/or received as shown by the shaded time slots. The channel can then be closed once analyte sensor system 8 and display device 14 determines that all requested data has been transmitted to the respective devices or it the transmission window time expires. At the start of a new $T_{update}$ interval, the process is repeated.

Continuously re-establishing a new communication channel to allow for partially or wholly powering down the transceiver 316 during each update interval $T_{update}$ can provide significant power savings and can allow the sensor electronics module 12 to operate continuously for six months or more without requiring a battery replacement. Furthermore, rather than blindly transmitting glucose data points during the transmission window $T_{window}$, communication channels may be established so that only the desired display devices 14 may receive the glucose information. This may prevent unauthorized use and interception of glucose measurement values. In addition, by establishing a secure two-way communication channel, requests for specific glucose measurement values or communication of calibration or configuration information may be transmitted on an as-needed/requested basis between the sensor system 8 and display device 14.

Also, in some embodiments, the communication window need not open during every update interval $T_{update}$. Instead, the window can open every second, third or fourth update interval $T_{update}$, for example, so that communication between the sensor system 8 with the display device 14 occurs less frequently than every update interval $T_{update}$. Doing so can further reduce power consumption. Accordingly, a window frequency variable $F_{window}$ can be used that dictates a frequency the window opens.

In some embodiments, the update interval $T_{update}$, transmission window $T_{window}$ and/or window frequency $F_{window}$ may be variable. $T_{update}$, $T_{window}$ and/or $F_{window}$ can be user configurable (e.g., by inputting a value for the variable using user interface of display device 14) and/or automatically varied by the sensor system 8 or display device 14 based on one or more criteria. The criteria can include: (i) a monitored battery power of the sensor system 8, (ii) a currently measured, previously measured and/or predicted glucose concentrations meeting or exceeding a predetermined threshold, (iii) a glucose concentration trend of the host based on currently measured, previously measured and/or predicted glucose concentrations, (iv) a rate of change of glucose concentration of the host based currently measured, previously measured and/or predicted glucose concentrations meeting or exceeding a predetermined threshold, (v) whether the host is determined to be in or near hyperglycemia based on currently measured, previously measured and/or predicted glucose concentrations, (vi) whether the host is determined to be in or near hypoglycemia based on currently measured, previously measured and/or predicted glucose concentrations, (vii) user inputted activity of the host (e.g., exercising or sleeping), (viii) time since a sensor session has started (e.g., when a new sensor 10 is used), (ix) one or more errors detected by sensor system 8 or display device 14, 16, 18, 20, and (x) type of display device.

$T_{update}$, $T_{window}$ and/or $F_{window}$ and other configuration items described herein may form part of a communication protocol profile that may be stored on any device that implements the fundamental communication protocol to allow for a customized use of the protocol for receiving glucose measurement values, such as sensor system 10 and display device 14.

Figure 10:
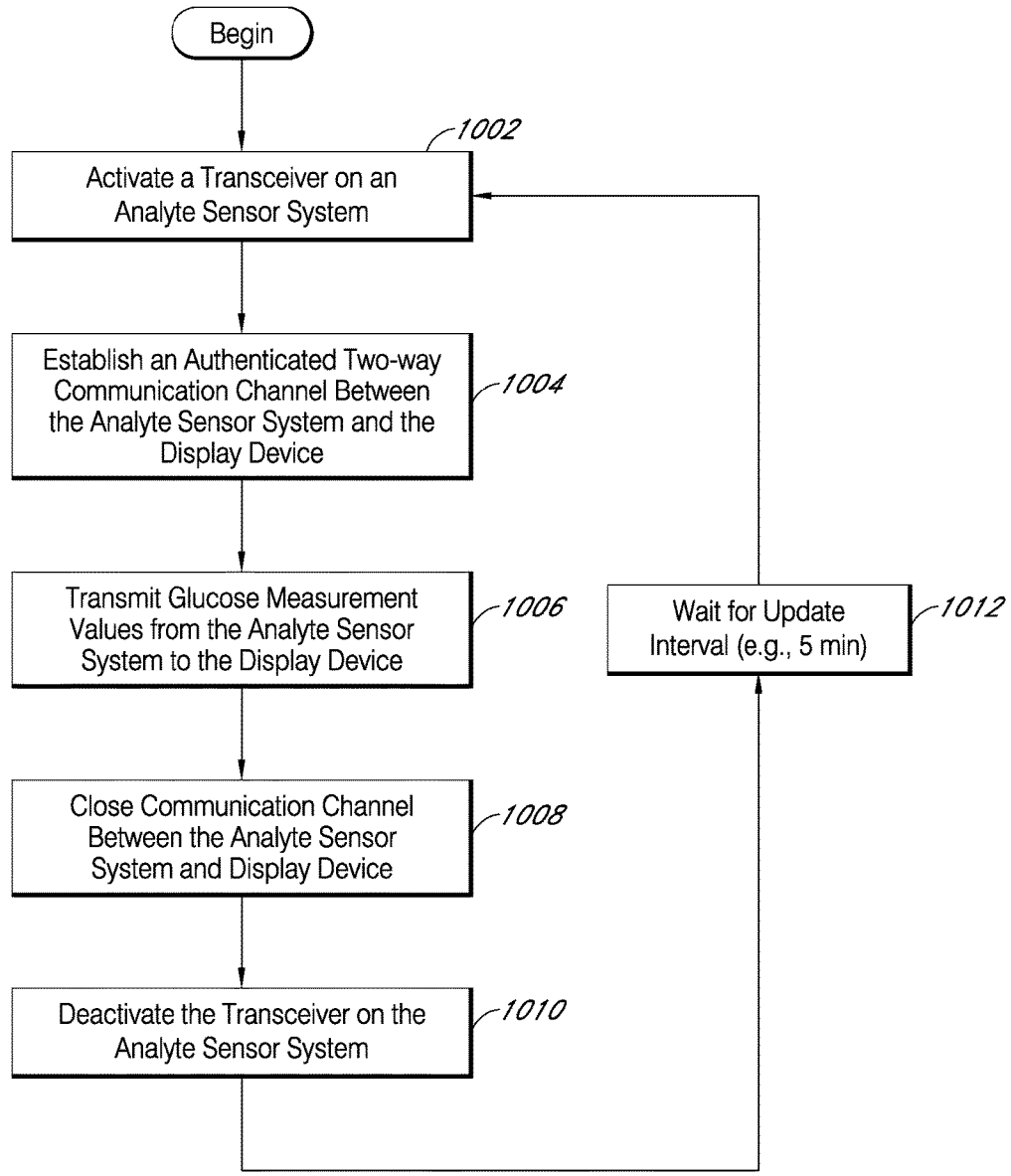
FIG. 10 is a flowchart of an exemplary method for sending glucose measurement values from an analyte sensor system to a display device.

FIG. 10 is a flowchart of an exemplary method for sending glucose measurement values from an analyte sensor system 8 to a display device 14. At a pre-determined time in an update interval $T_{update}$, an analyte sensor system 8 may activate a transceiver 316 as shown in block 1002. This may include powering the transceiver 316 or awakening the transceiver 316 from a low power mode/state such as a sleep mode. In block 1004, the transceiver 316 may open and establish an authenticated two-way communication channel between the analyte sensor system 8 and a display device 14. If the channel is established, in block 1006, the analyte sensor system 8 and the display device 14 may transmit information between them, either automatically (e.g., device determines a triggering event to transmit specific information) or in response to a request received from the other device. Such information can include one or more glucose measurement values, calibration information, alert settings, communication synchronization information, and the like. Once the transmission is complete and data requested by the display device 14 and sensor system 10 is sent, the analyte sensor system 8 may close the communication channel. In block 1010, the analyte sensor system 8 may deactivate the transceiver 316 such as powering-down the transceiver or causing it to go into a low power mode. The operations in block 1004 through 1008 may be repeated with additional display devices until the transmission window $T_{window}$ closes. The analyte sensor system 8 may then wait for the next transmission window $T_{window}$ to open as shown in block 1012, and in the meantime gather glucose measurement values, before the process is repeated continuously over the duration of a sensor session (e.g., corresponding to the life of non-durable sensor). Between each transmission window $T_{window}$, a new analyte sensor measurement may be obtained and stored for transmission.

User-initiated Switching on Sensor Electronics Via NFC

As described above, in some embodiments, sensor electronics module 12 may be automatically switched from a low power mode (e.g., power off mode or low power storage mode) to a higher power operational mode when the sensor electronics module is attached to a disposable sensor. In at least some of these embodiments, the initialization or run-in process may take time to ensure that the sensor is stable before allowing the sensor to make and/or transmit measurements.

In other embodiments, the user may switch the mode of the transceiver 316 from a low power mode to a higher operational power mode. For example, in some embodiments, it may be advantageous to allow the user to wake the analyte sensor system 8 from its storage mode.

In some embodiments, analyte sensor system 8 further includes near field communication (NFC) capability. In some embodiments, an NFC tag is integral to the electronics in sensor system 8 (shown as NFC tag 322 in FIG. 3) or embedded in e.g., the housing or mounting unit 240. While not shown explicitly, NFC tag 322 may be included as part of transceiver 316, making transceiver 316 a "smart transceiver".

As can be appreciated, NFC is a set of short-range wireless technologies, typically requiring a distance of 10 cm or less. Currently, NFC operates at 13.56 MHz on ISO/IEC 18000-3 air interface and at rates ranging from about 106 kbit/s to 424 kbit/s. NFC generally includes an initiator and a target, where the initiator actively generates a radio frequency (RF) field that can power a passive target.

In some embodiments, analyte sensor system 8 corresponds to the NFC target and a display device 14 such as a mobile phone (e.g., smartphone) capable of NFC communication corresponds to the NFC initiator. In such embodiments, the smartphone may include a software application or "app" that can be used for communication with analyte sensor system 8. In some embodiments, the smartphone app may be configured to prompt the user to enter information specific to sensor system 8 (e.g., transmitter serial number) to wake the electronics module 12 out of storage mode. Thereafter, the smartphone app may activate the NFC functionality and instruct the user to hold the smartphone in close proximity (e.g., within 1 ft.) to the sensor system 8.

In some embodiments, the smartphone provides energy to NFC tag 322 by generating an RF field. The smartphone may also transmit e.g., identification information, and a command for the electronics module 12 to wake out of storage mode. It should be appreciated that the identification information may be specific to the sensor system 8 and serve as a validation that the NFC process is authenticated. In some alternate embodiments, the smartphone may read the e.g., transmitter serial number from the NFC tag 322, automatically enter it into the application, and proceed with the wake up process.

Once NFC tag 322 has received the correct wake up command, it can send a signal to an interrupt input on processor 314. After processor 314 has received the interrupt, the processor 314 may exit the low-power sleep mode and begin the normal operation of the sensor system 8, within minimal delay.

Because of the short communication range, NFC activation may inherently provide good security for activating the sensor system 8. Additionally, the use of a specific unique transmitter ID and a wake command add further security to the activation process.

In some embodiments, reading the transmitter ID from NFC tag 322 may be used for pairing electronics module 12 that is already awake to a receiving device such as a laptop or another smartphone. Such a pairing process is described below.

Pairing of Two or more Devices

In some embodiments, pairing of two devices (e.g., a master and slave device) may be required to establish a relationship between two devices that want to communicate with one another. Pairing may be accomplished during the channel establishment process described above between the two devices. Establishing a channel may involve broadcasting a unique ID by one device and a search and acquisition of this ID by another device.

A parameter that may be used in device pairing is the master device ID. In order to establish a communication channel, a master transmitter may broadcast its device ID (along with some other information) in the above described beacon and the receiver checks for the presence of the device ID of the transmitter with which it wants to communicate in the received beacons. The device ID may be a 2-byte value representing a specific master device, for example.

Although a master device ID may provide some level of security, in that a slave device can be programmed to communicate only with a master device having a particular device ID number, additional security can be useful in some embodiments. As described above, to save power by deactivating the transceiver 316 of the analyte sensor system 8, a communication channel may be re-established during each update interval $T_{update}$. As such, as part of the channel establishment process, regular and repeated re-authentication may also be provided.

To provide additional security, some embodiments of the present invention can use two pieces of information to pair a receiver with a particular transceiver device. These two pieces of information include the device ID described above and another value which is referred to herein as a sensor security code. The device ID is used as described above to e.g., filter receipt of non-matching messages at the lowest layer of the protocol stack. The sensor security code is used for e.g., a key based authentication scheme at the software application layer of the system. In some embodiments, both the device ID and the sensor security code can be derived from an identifier (e.g., a manufacturer's serial number) associated with the sensor system 8.

As seen in the embodiment of FIG. 1, the sensor system 8 comprises two fundamental components, the continuous sensor 10 and the electronics module 12. These two components may be separable from one another, allowing, for example, replacement of the continuous sensor portion 10. In this case, the identifier may be etched into, printed on or otherwise attached to a housing of the electronics module portion 12.

The sensor system 8 may include seven alphanumeric characters printed on a housing of the sensor system 8, which can comprise the identifier used for identification purposes. This alphanumeric series of characters may be used to generate both the device ID used in the master beacons to establish a channel and to generate the sensor security code used for additional security in the glucose monitoring system.

NFC and Window Transitioning

As explained above, in some embodiments, it may be desirable to allow the user to wake up or turn on electronics module 12. As presented above, the transceiver 316 may be off while in storage mode or in between transmission windows (e.g., where the transceiver 316 communicates with another device 14 every 5 minutes).

NFC wake up can cause immediate or forced communication between electronics module 12 and e.g., a smartphone or other device. Such forced communication can occur as described above, such as when a user uses a smartphone application to wake up the electronics module 12. It can be appreciated that the forced wake up would often be out of sync with the normal communication window (e.g., every 5 minutes). Thus, in some embodiments, the forced wake up can cause the transmission window to start over at the time the forced communication commences. In other embodiments, the forced wake up can cause a break or gap in the transmission window, but does not cause the transmission window to start over. Further description on transmission window initialization and communication is provided below.

Several benefits may be realized from NFC forced wake up that is out of sync with the normal transmission window. For example, such NFC wake up may be used to cause information to be sent almost immediately (e.g., in real-time), such as: transfer a calibration value to the sensor system 8 (e.g., at transceiver 316) and get an updated estimated glucose value (EGV) back to the display device (e.g., at transceiver 338), send down new settings (e.g., alarm settings, calibration settings, etc.) to the sensor system 8, pair a display device 14 to the sensor system 8. In some embodiments, NFC wake up make also be used to enable test modes and code upgrades.

As described above, the NFC forced wake up may allow the pairing of electronics module 12 of sensor system 8 with another display device 14 such as a smartphone. This pairing may be done without requiring a mechanical button, such as is necessary for e.g., Bluetooth pairing.

While immediate communication using NFC has generally been referred to as NFC wake up, it should be appreciated that if the communicating devices are already awake, that wake up is not necessarily performed. Rather, in such embodiments, the communication is a forced communication that sends some sort of immediate data, such as a calibration value. For example, in some embodiments, NFC may be used to start the initialization period when a new sensor 10 is attached to sensor system 8. This may allow initialization to begin immediately regardless of where the transmission window is (e.g., when the next transmission window will begin).

Transmission Pause or Low Transmission Power Mode

In some embodiments, it may be desirable to allow a user to cause electronics module 12 to enter a transmission suspended or pause mode. Such transmission pause mode may be useful during times when a user may be prohibited from transmitting data, such as on an airplane. Such a mode may allow a user to not have to power down analyte measurement functions of the electronics module 12, but instead, the electronics module 12 is suspended from transmitting information for a duration of time.

In some embodiments, a user may initiate a "transmission pause mode" request in a software application on their display device 14 such as a smartphone when the user is in the airport or on an airplane. The smartphone may prompt the user to enter the estimated duration e.g., of the flight or time T. The smartphone may thereafter send a command to the electronics module 12 to enter into the "transmission pause mode" for a certain time duration, e.g., time T.

Upon receiving the "airplane mode" command, electronics module 12 may be configured to decrease its RF transmission power for the duration of time T. In some embodiments, after time T has elapsed, electronics module 12 returns to its normal RF power level and resumes normal operation.

A benefit of having an "transmission pause mode" is that electromagnetic energy produced by sensor system 8 may be minimized during a flight (e.g., minimizing any interference of airplane electronic systems due to radio transmissions from the sensor electronics module).

In some embodiments, "transmission pause mode" may be implemented using NFC. In some embodiments, a user may wake electronics module 12 from the "transmission pause mode" using NFC, such as by selecting a menu option on display device 14 to exit pause mode and subsequently tapping sensor electronics module, which initiates an NFC instruction for the sensor electronics module 12 to wake up.

In some implementations, once the transmission pause mode is exited, sensor data generated while in the pause mode can then be transmitted to display device 14 to fill any gaps in sensor data. Such a "backfill" of data can be performed automatically, without requiring any user direction.

Further, in circumstances where transmission may be allowed but at a lower transmission power, such as on some airplanes, a user can cause one or both of electronics module 12 and display device 14 to wirelessly transmit using a lower power transmission mode in accordance with some implementations. That is, one or both of the sensor electronics module 12 and display device 14 transmit using less power than during normal operation. While transmitting with less power may decrease the range of transmission between devices, it is believed that a user on an airplane, for example, will likely have the devices in relatively close proximity so as to not need the higher transmission power any way.

In some implementations, the power for transmission during the low transmission power mode in the range of 25% to 75%, such as about 25%, 35%, 50%, 60% or 75%, as compared to the transmission power used during normal operation.

In some implementations, the "low transmission power" mode can be implemented by a user in the same manner described above with respect to the "transmission pause" mode (e.g. entering a time T for transmitting in low power mode or using NFC to exit low transmission power mode), but instead of pausing all transmission, the sensor electronics module 12 and display device 14 transmit using less power. Further, because the sensor electronics module 12 and display device 14 still communicate during low transmission mode (as opposed to implementations of the pause mode), in some implementations a user can exit the low transmission power mode by selecting a command using the display device, which subsequently causes the display device to exit the low transmission power mode and instructs the sensor electronics module to exit the low transmission mode in the next communication cycle, for example.

Adjustable Integration Window

The information communicated from the sensor system 8 to display device 14 generally includes or relates to sensor data. In one example, the sensor data comprises digital data in "counts" converted by an A/D converter from an analog signal (e.g., voltage or amps) and includes one or more data points representative of a glucose concentration. Sensor data may include a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period, or integration window.

As described elsewhere herein, for sensor calibration, a user may input or enter a reference value at some point in time. For purposes of illustration, the following explanation uses a blood glucose value (BGV) as the reference value, although it is understood that other measurements can be used as a reference value instead. In some embodiments, a calibration algorithm will then match or pair the BGV with the last available integrated sensor signal or value to calibrate the data set. In some embodiments, a calibration algorithm will then match or pair the BGV with an integrated sensor signal having a time stamp that is proximate to the time stamp of the BGV to calibrate the data set. Accordingly, the time difference between the entered BGV and the last available integrated sensor value could be the maximum time between the transmission windows (e.g., 5 minutes). In addition to this time difference, the integrated sensor signal or value may be delayed itself due to processing lag time due to filtering and the like. For example, the integrated sensor signal may have a delay of 2.5 minutes because of data filtering, making a potential time delay about 7.5 minutes. It can be appreciated that a time difference or delay can have a negative impact on system accuracy, as the physiological glucose level may have changed during that time, especially in the case of when the system is calibrated when the physiological glucose level is changing rapidly.

In some embodiments, to provide an improved match between the BGV and integrated sensor signal, the integrated sensor signal may be provided "on demand" or in real-time (e.g., at the point in time when user enters a BGV for calibration). In some embodiments, the integrated sensor signal may be provided using software (e.g., one or more algorithms) that records and/or manipulates sensor signal data.

For example, in some embodiments, the sensor signal may be captured and integrated every 30 seconds. Every 5 minutes, ten of these 30 second values are averaged to provide an integrated sensor signal to the algorithm. The collected sensor signals and integrated values may be stored for example, in a memory buffer which may be part of e.g., memory 318. It should be appreciated that the integration value parameters used are exemplary only, and that any sampling duration and sampling number is contemplated.

To provide an integrated sensor signal when a BGV is entered, the integration window (and hence the values used for providing the integrated sensor signal) may need to be shifted. This integration window shifting or adjusting may be achieved by: (1) storing the last ten 30 second data points in a memory buffer; (2) when a new 30 second data point comes in, entering the new data point in the buffer and deleting the oldest data point; and (3) when a calibration or BGV is entered, calculating the integrated sensor signal on the most recent data point values stored in the buffer. In the present example, a 5 minute averaged sensor signal can be provided that is matched within 30 seconds of the entered calibration value, thereby yielding improved accuracy. In some embodiments, the accuracy of the averaged sensor signal can be confirmed by comparing a time stamp associated with the integration value to the time stamp associated with the entered calibration value.

While the example provides using ten 30 second values, any number of samples or data points for any duration of time that results in an integration window of a fixed period may be used. However, having the values selected from integration window shifted to be closer to the calibration value will generally be more representative of the BGV. For example, in some embodiments, the averaging of the integrated sensor signal may be performed or centered around the entered glucose value (e.g., taking the five 30 second points before the BGV and the five 30 second points after the BGV). Centering the integration sensor signal around the BGV may result in minimizing any time delay present in the averaged five minute value.

Also, in some embodiments, a weighted average that is more favorably or heavily weighted on the data point(s) in time closest to the entered BGV may be used. In some embodiments, additional tools such as adaptive filtering may be used to monitor the noise of the points.

In addition or instead of using data values stored in the memory buffer, the integrated sensor signal or value may be extrapolated using e.g., at least one or more values stored in the memory buffer. In some examples, the integrated sensor signal may be extrapolated to a point of 2.5 minutes in the future using five 30 second data values stored in the buffer. In other embodiments, the integrated sensor signal may be extrapolated to a point of 2.5 minutes in the future using the rate of change on the previous sampled data points.

In some embodiments, to improve the accuracy of matching the entered glucose values with the integrated sensor signals, a time stamp may be provided with the glucose values. The algorithm may use the time stamp associated with a BGV to determine which set of data (e.g., which 10 points) need to be averaged to yield an integrated sensor signal that is matched or paired with the glucose value. In preferred embodiments, the sensor system 8 and paired device 14 in communication with each other are synchronized, thereby ensuring proper interpretation of time stamps.

In some embodiments, when there is a delay in communication between the paired device 14 and sensor system 8, the buffer can be configured to store more integrated sensor signals. For example, if there is a 5 minute delay in communication, the buffer may be configured to store the present integrated sensor signal and a past integrated sensor signal or a total of 20 30 second values.

Also, while the integration window may remain a fixed duration (e.g., 5 minutes), the data presentation on paired device 14 does not need to be limited to one point for the fixed duration. For example, if it is desired to have the glucose values displayed within 2.5 minute intervals, every 2.5 minutes the last ten 30 second values may be averaged and fed into an integration algorithm, thereby providing a moving average.

Other tools or strategies for improving the time lag and accuracy of the sensor system 8 include using adaptive sampling. For example, as the glucose rate of change increases, the sampling rate can also increase (e.g., shorter sample times or shorter integration window, greater number of samples, etc.).

Embodiments of the present disclosure are described above and below with reference to flowchart illustrations of methods, apparatus, and computer program products. It will be understood that each block of the flowchart illustrations, and combinations of blocks in the flowchart illustrations, can be implemented by execution of computer program instructions. These computer program instructions may be loaded onto a computer or other programmable data processing apparatus (such as a controller, microcontroller, microprocessor or the like) in a sensor electronics system to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks presented herein.

Methods and devices that are suitable for use in conjunction with aspects of the preferred embodiments are disclosed in U.S. Pat. Nos. 4,757,022; 4,994,167; 6,001,067; 6,558, 321; 6,702,857; 6,741,877; 6,862,465; 6,931,327; 7,074, 307; 7,081,195; 7,108,778; 7,110,803; 7,134,999; 7,136, 689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206,297; 8,216,139; 8,229,534; 8,229,535; 8,229,536; 8,231,531; 8,233,958; 8,233,959; 8,249,684; 8,251,906; 8,255,030; 8,255,032; 8,255,033; 8,257,259; 8,260,393; 8,265,725; 8,275,437; 8,275,438; 8,277,713; 8,280,475; 8,282,549; 8,282,550; 8,285,354; 8,287,453; 8,290,559; 8,290,560; 8,290,561; 8,290,562; 8,292,810; 8,298,142; 8,311,749; 8,313,434; 8,321,149; 8,332,008; 8,346,338; 8,364,229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S.

Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; U.S. Patent Publication No. 2005-0182451-A1; U.S. Patent Publication No. 2013000536650A1; and U.S. Patent Publication No. 2013-0053666-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYS- TEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS"; U.S. application Ser. No. 13/779,607 filed on Feb. 27, 2013 and entitled "ZWITTERION SURFACE MODIFICATIONS FOR CONTINUOUS SENSORS"; U.S. application Ser. No. 13/780,808 filed on Feb. 28, 2013 and entitled "SENSORS FOR CONTINUOUS ANALYTE MONITORING, AND RELATED METHODS"; U.S. application Ser. No. 13/784,523 filed on Mar. 4, 2013 and entitled "ANALYTE SENSOR WITH INCREASED REFERENCE CAPACITY"; U.S. application Ser. No. 13/789,371 filed on Mar. 7, 2013 and entitled "MULTIPLE ELECTRODE SYSTEM FOR A CONTINUOUS ANALYTE SENSOR, AND RELATED METHODS"; U.S. application Ser. No. 13/789,279 filed on Mar. 7, 2013 and entitled "USE OF SENSOR REDUNDANCY TO DETECT SENSOR FAILURES"; U.S. application Ser. No. 13/789,339 filed on Mar. 7, 2013 and entitled "DYNAMIC REPORT BUILDING"; U.S. application Ser. No. 13/789,341 filed on Mar. 7, 2013 and entitled "REPORTING MODULES"; U.S. application Ser. No. 13/790,281 filed on Mar. 8, 2013 and entitled "SYSTEMS AND METHODS FOR MANAGING GLYCEMIC VARIABILITY"; U.S. application Ser. No. 13/796,185 filed on Mar. 12, 2013 and entitled "SYSTEMS AND METHODS FOR PROCESSING ANALYTE SENSOR DATA"; U.S. application Ser. No. 13/796,642 filed on Mar. 12, 2013 and entitled "SYSTEMS AND METHODS FOR PROCESSING ANALYTE SENSOR DATA"; U.S. application Ser. No. 13/801,445 filed on Mar. 13, 2013 and entitled "SYSTEMS AND METHODS FOR LEVERAGING SMARTPHONE FEATURES IN CONTINUOUS GLUCOSE MONITORING"; U.S. application Ser. No. 13/802,424 filed on Mar. 13, 2013 and entitled "SYSTEMS AND METHODS FOR LEVERAGING SMARTPHONE FEATURES IN CONTINUOUS GLUCOSE MONITORING"; U.S. application Ser. No. 13/802,237 filed on Mar. 13, 2013 and entitled "SYSTEMS AND METHODS FOR LEVERAGING SMARTPHONE FEATURES IN CONTINUOUS GLUCOSE MONITORING"; and U.S. application Ser. No. 13/802,317 filed on Mar. 13, 2013 and entitled "SYSTEMS AND METHODS FOR LEVERAGING SMARTPHONE FEATURES IN CONTINUOUS GLUCOSE MONITORING".

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for transmitting data between devices of an analyte monitoring system, the method comprising:
    generating sensor data using a sensor electronics module electrically connected to a continuous analyte sensor;
    establishing a two-way communication channel between the sensor electronics module and a display device, wherein each of the sensor electronics module and the display device transmit via a first transmission mode at a first transmission power, wherein the transmission includes sending a portion of the sensor data from the sensor electronics module to the display device;
    initiating a low power transmission mode responsive to sensing user input at a user interface of the display device indicative of entering the low power transmission mode, wherein the low power transmission mode comprises the sensor electronics module transmitting another portion of the sensor data to the display device at a second transmission power that is lower than the first transmission power;
    exiting the low power transmission mode upon receiving instructions via a short-range communication protocol, that is different from the first transmission mode and the low power transmission mode, and transitioning to the first transmission mode upon exiting the low power transmission mode.

2. The method of claim 1, wherein the user input comprises sensing user selection of a user-selectable button on the user interface of the display device.

3. The method of claim 1, wherein the second transmission power is in a range of about 25%-75% lower than the first transmission power.

4. The method of claim 1, wherein the transmission via the first transmission mode occurs when the sensor electronics module is at a first distance from the display device.

5. The method of claim 4, wherein the transmission via the low power transmission mode occurs when the sensor electronics module is at a second distance from the display device, and wherein the second distance is shorter than the first distance.

6. The method of claim 1, further comprising resuming the transmitting of sensor data at the first transmission power upon the transition to the first transmission mode from the low power transmission mode.

7. The method of claim 1, wherein the instructions to exit the low power transmission mode are generated responsive to the user input on the user interface of the display device.

8. A system for monitoring analyte concentration data of a host, comprising:
    a continuous analyte sensor;

a sensor electronics module configured to electrically couple to the analyte sensor and generate analyte sensor data using the continuous analyte sensor; and a display device configured to wirelessly receive information indicative of the analyte sensor data from the sensor electronics module, wherein the sensor electronics module and the display device are configured to establish a two-way communication channel between the sensor electronics module and the display device, wherein each of the sensor electronics module and the display device transmit at a first transmission power during a normal operating mode, wherein the transmission includes sending a portion of the sensor data from the sensor electronics module to the display device, and wherein the sensor electronics module is configured to:

transmit another portion of the sensor data to the display device at a second transmission power that is lower than the first transmission power during a low power transmission mode that is initiated responsive to receiving user input at user interface of the display device indicative of entering the low power transmission mode, exit the low power transmission mode upon receiving instructions via a short-range communication protocol, that is different from the normal operating mode and the low power transmission mode, and transition to the normal operating mode upon the exit from the low power transmission mode.

9. The system of claim 8, wherein the user input comprises sensing user selection of a user-selectable button on the user interface of the display device.

10. The system of claim 8, wherein the low power transmission mode is in a range of about 25%-75% lower than the normal operating mode.

11. The system of claim 8, further configured to resume the transmission of sensor data at the first transmission power upon the transition to the normal operating mode from the low power transmission mode.

12. The system of claim 8, wherein the instructions to exit the low power transmission mode are generated responsive to user input on the user interface of the display device.

* * * * *

UNITED STATES PATENT AND TRADEMARK OFFICE
CERTIFICATE OF CORRECTION

PATENT NO. : 9,931,036 B2
APPLICATION NO. : 14/142677
DATED : April 3, 2018
INVENTOR(S) : Thomas Miller et al.

Page 1 of 1

It is certified that error appears in the above-identified patent and that said Letters Patent is hereby corrected as shown below:

In the Specification

In Column 4 at Line 57, Change "the a" to --the--.

In Column 5 at Line 62, Change "en" to --an--.

In Column 25 at Line 54, After "system" insert --.--.

Signed and Sealed this
Twenty-sixth Day of June, 2018

Andrei Iancu
*Director of the United States Patent and Trademark Office*